United States Patent [19]
Bell et al.

[11] Patent Number: 5,114,711
[45] Date of Patent: May 19, 1992

[54] COVALENTLY LINKED POLYPEPTIDE CELL MODULATORS SUCH AS INTERFERON-LYMPHOTOXIN CONJUGATES

[75] Inventors: Leslie D. Bell, Thame; Keith G. McCullagh, Princes Risborough; Alan G. Porter, High Wycombe, all of United Kingdom

[73] Assignee: G. D. Searle & Co., Chicago, Ill.

[21] Appl. No.: 379,509

[22] Filed: Jul. 13, 1989

Related U.S. Application Data
[63] Continuation of Ser. No. 803,748, Dec. 2, 1985, Pat. No. 4,935,233.

[51] Int. Cl.$^5$ .............. A61K 37/66; A61K 39/44; C07K 15/26; C07K 17/02
[52] U.S. Cl. .............. 424/85.1; 424/85.2; 424/85.4; 424/85.5; 424/85.6; 424/85.7; 424/85.8; 530/351; 530/395; 530/405; 530/409; 530/391.1; 530/391.7; 530/391.9; 530/388.23; 530/389.2; 514/2; 514/8; 514/12; 514/21; 930/142; 930/143
[58] Field of Search .............. 530/351, 388, 405, 409, 530/395; 424/85.1, 85.2, 85.4, 85.5, 85.6, 85.7, 85.8; 930/142, 143; 514/2, 8, 12, 21

[56] References Cited

U.S. PATENT DOCUMENTS
Re. 32,637  4/1988  Ishida .............. 530/350
4,468,382  8/1984  Bacha et al. .

FOREIGN PATENT DOCUMENTS
141484   5/1985   European Pat. Off. .
158198  10/1985   European Pat. Off. .
237019   9/1987   European Pat. Off. .
051146249 7/1983  World Int. Prop. O. .
8502198  5/1985   World Int. Prop. O. .

OTHER PUBLICATIONS
Rudinger in J. A. Parsons ed *Peptide Hormones* Univ. Park Press Baltimore, Jun. 1976 pp. 1–7.
CA 106(9):159 abstract #62196j.
Shepard et al (1984) Nature 294:563–565.

*Primary Examiner*—Christine Nucker
*Assistant Examiner*—Kay Kim
*Attorney, Agent, or Firm*—Mary Jo Kanady; Paul D. Matukaitis

[57] ABSTRACT

Described is a new class of polypeptide cell modulators characterized by being composed of two covalently linked cell modulators in a linear polypeptide sequence. Such dual function polypeptides have new and particularly useful activities when the component polypeptide cell modulators are interferons, lymphokines or cytotoxins which act through different and specific cell receptors to initiate complementary biological activities.

30 Claims, 19 Drawing Sheets

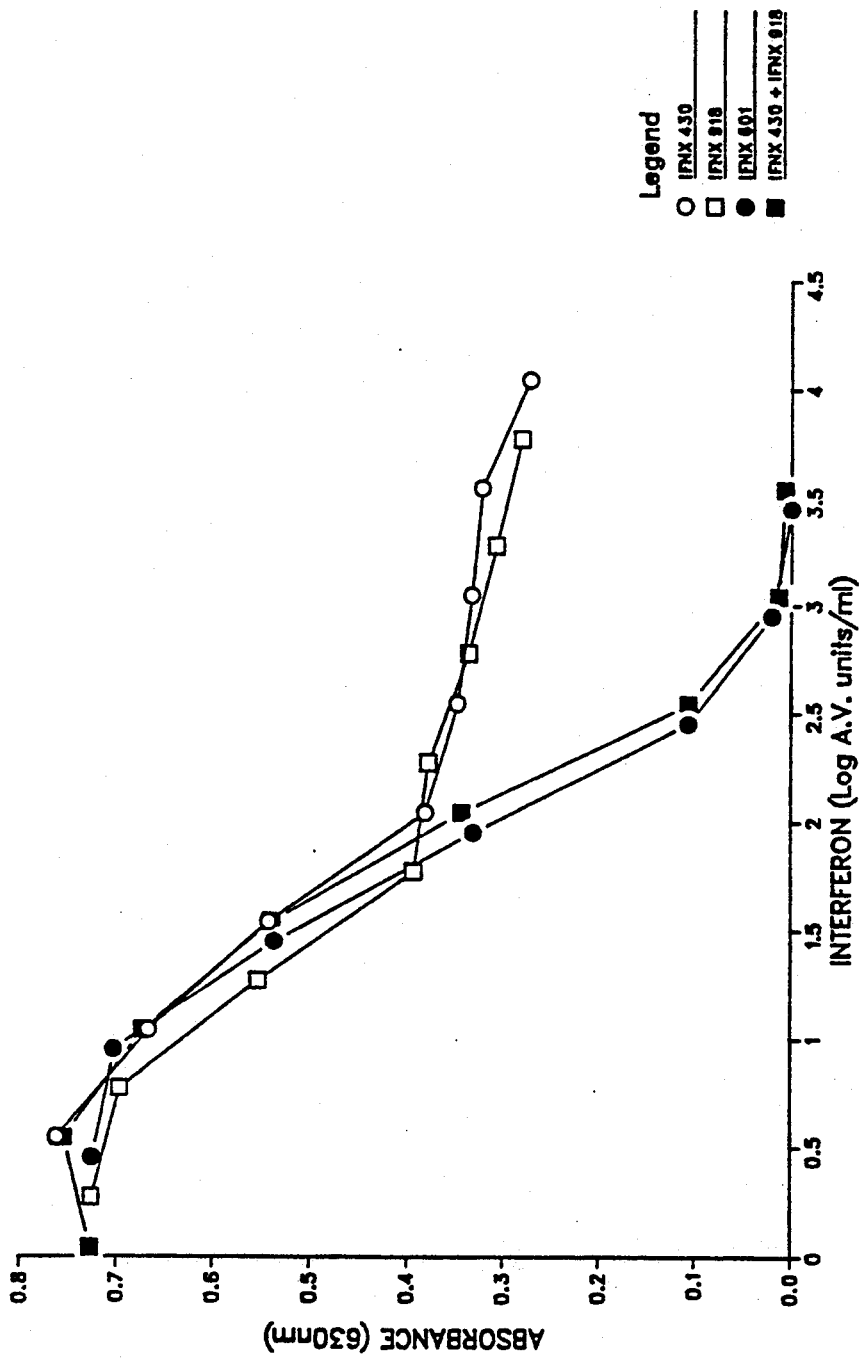

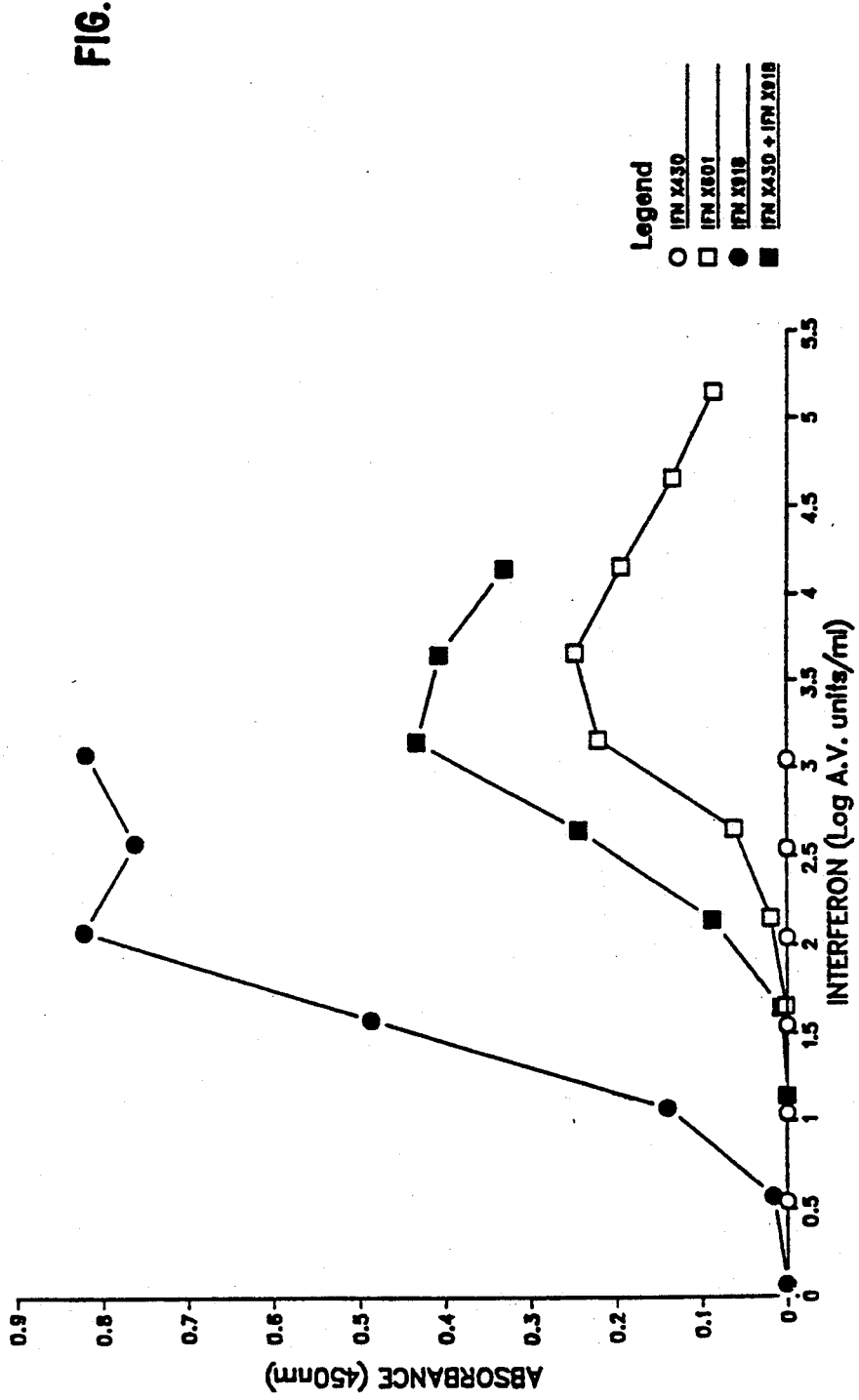

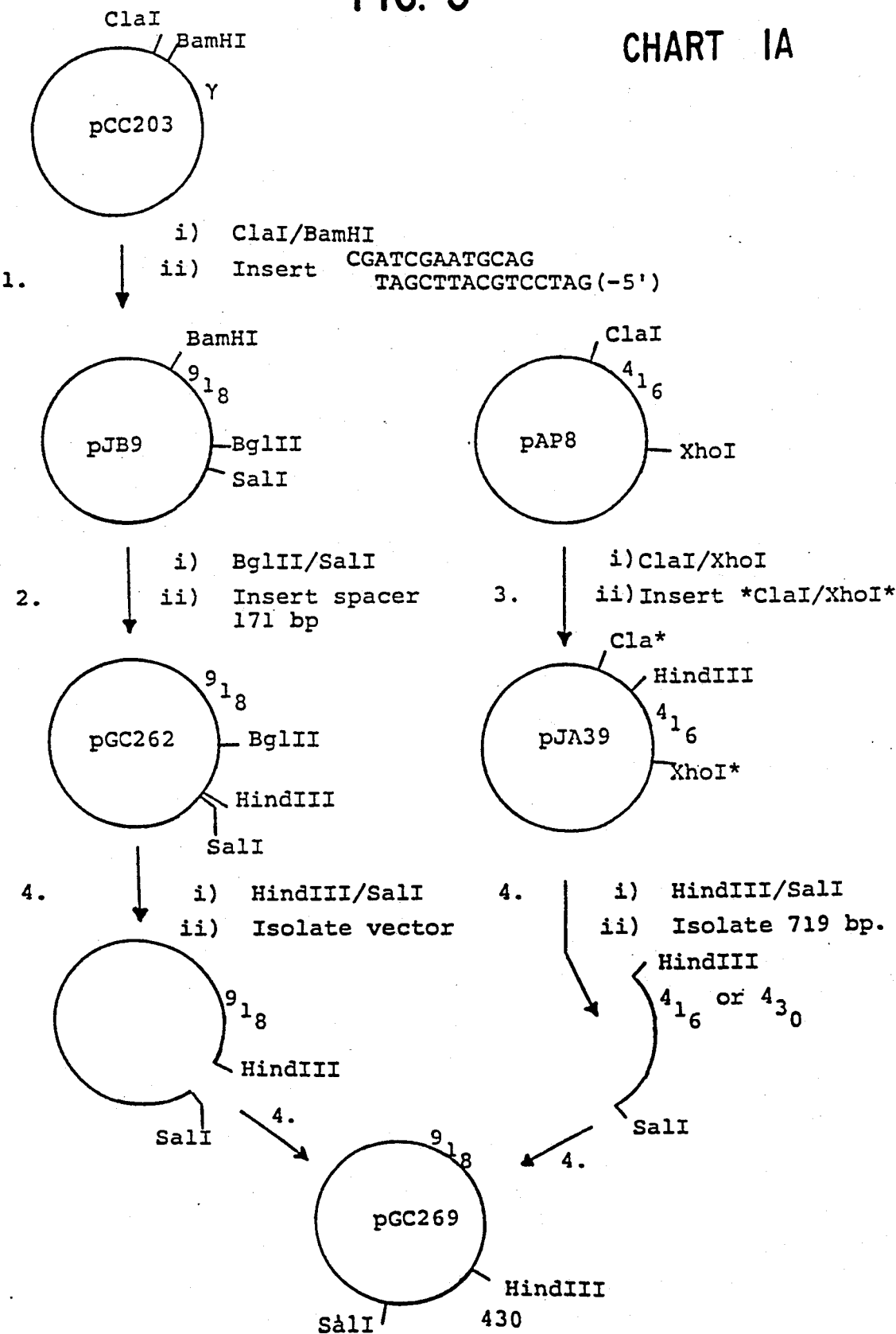

FIG. 4

CHART 1Aa

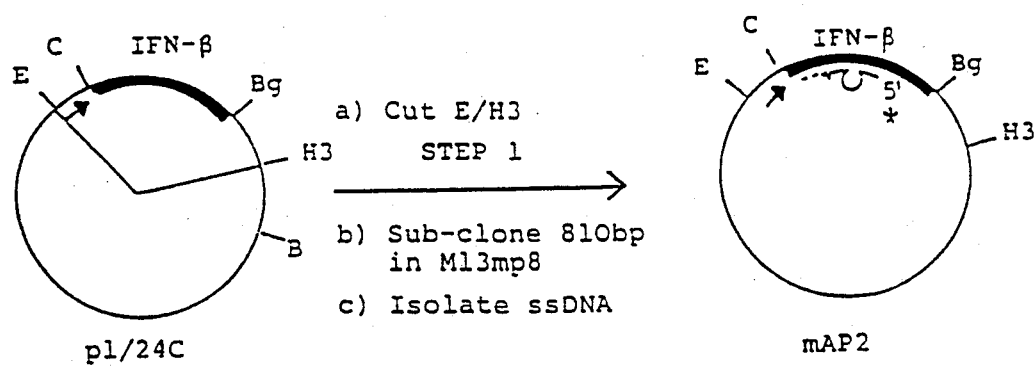

a) Cut E/H3    STEP 1 b) Sub-clone 810bp in M13mp8 c) Isolate ssDNA pl/24C → mAP2 a) Anneal mismatch primer *
 *5'-CAGTGCTCGAGGAATCTTGTC-3',
 pol.I fill, ligate, transform
 E.coli JM101 b) Grow in shake flask, isolate
 plasmid DNA, check partially
 cut with XhoI  (C↓TCGAG)

STEP 2

Mixture of:-

|  | 74 | 75 | 76 | ←CODON |
|---|---|---|---|---|
| Mutant sequence | TCC. | TCG. | AGC. | |
| Wild type sequence | TCA. | TCT. | AGC. | |
| | --Ser-Ser-Ser-- | | | |

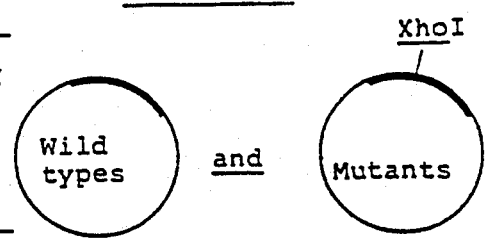

Wild types and Mutants a) Cut (partially) XhoI, isolate linear DNA b) Religate, transform E.coli JM101, check all clones cut with XhoI

STEP 3 mAP3

CHART 1Ab

Key: E=EcoRI; C=ClaI; Bg=BglII; H3=HindIII; B=BamHI; X=XhoI; ↗ trp promoter

FIG. 7    CHART 2

A.

```
        BglII
          ↓
   AGATCTCAGATGCTGTTTCGTGGTCGCCGTGCTTCTCAGGAACCGTCTGGTCCAATCTCTACTATCAACCCGTCTCCTCC
   TCTAGAGTCTACGACAAAGCACCAGCGGCACGAAGAGTCCTTGGCAGACCAGGTTAGAGATGATAGTTGGGCAGAGGAGG

GTCTAAAGAATCTCATAAATCTCCAATGAGCTACAACTTGCTTGGATTCCTACAAAGAAGCAGCAATTTCAGTGTCAGA
   CAGATTTCTTAGAGTATTTAGAGGTTACTCGATGTTGAACGAACCTAAGGATGTTTCTTCGTCGTTAAAAGTCACAGTCT
   HindIII
      ↓AGCTTTAGAAAGTCGAC
       TCGAAATCTTTCAGCTG
                    ↑
                   SalI
```

***************************************

B.

```
        BglII
          ↓
   AGATCTCAGATGCTGTTTCGTGGTCGCCGTGCTTCTCAGGCAGGTTCTGCAGGCTCCGCTGGCTCCGCAGGTTCCGCTGG
   TCTAGAGTCTACGACAAAGCACCAGCGGCACGAAGAGTCCGTCCAAGACGTCCGAGGCGACCGAGGCGTCCAAGGCGACC

TTCTGCGGGCTCTGCGAGGCTCTATGAGCTACAACTTGCTTGGATTCCTACAAAGAAGAGCAGCAATTTCAGTGTCAGAAGC
   AAGACGCCCGAGACGTCCGAGATACTCGATGTTGAACGAACCTAAGGATGTTTCTTCGTCGTTAAAAGTCACAGTCTTCG
                                                                              ↑HindIII
   TTTAGAAAGTCGAC
   AAATCTTTCAGCTG
              ↑
             SalI
```

CHART 3  IFNX 601

```
              5                    10                     15
MET-GLN-ASP-PRO-TYR-VAL-LYS-GLU-ALA-GLU-ASN-LEU-LYS-LYS-TYR-
ATG CAG GAT CCA TAC GTT AAA GAA GCT GAA AAC CTG AAA AAA TAC 20                   25                     30
PHE-ASN-ALA-GLY-HIS-SER-ASP-VAL-ALA-ASP-ASN-GLY-THR-LEU-PHE-
TTC AAC GCA GGT CAC TCT GAC GTA GCA GAC AAC GGT ACC CTG TTC 35                   40                     45
LEU-GLY-ILE-LEU-LYS-ASN-TRP-LYS-GLU-GLU-SER-ASP-ARG-LYS-ILE-
CTC GGT ATC CTG AAA AAC TGG AAA GAA GAA AGC GAT CGT AAA ATC 50                   55                     60
MET-GLN-SER-GLN-ILE-VAL-SER-PHE-TYR-PHE-LYS-LEU-PHE-LYS-ASN-
ATG CAG TCT CAG ATC GTA TCT TTC TAC TTC AAG CTG TTC AAA AAC 65                   70                     75
PHE-LYS-ASP-ASP-GLN-SER-ILE-GLN-LYS-SER-VAL-GLU-THR-ILE-LYS-
TTC AAA GAT GAT CAG TCG ATC CAA AAA TCC GTT GAA ACT ATC AAA 80                   85                     90
GLU-ASP-MET-ASN-VAL-LYS-PHE-PHE-ASN-SER-ASN-LYS-LYS-LYS-ARG-
GAA GAC ATG AAC GTA AAA TTC TTC AAC TCT AAC AAA AAG AAG CGC 95                   100                    105
ASP-ASP-PHE-GLU-LYS-LEU-THR-ASN-TYR-SER-VAL-THR-ASP-LEU-ASN-
GAT GAC TTT GAA AAA CTG ACT AAC TAC TCG GTG ACC GAC CTG AAC 110                  115                    120
VAL-GLN-ARG-LYS-ALA-ILE-HIS-GLU-LEU-ILE-GLN-VAL-MET-ALA-GLU-
GTA CAG CGT AAA GCT ATC CAC GAG CTC ATT CAG GTT ATG GCA GAA 125                  130                    135
LEU-SER-PRO-ALA-ALA-LYS-THR-GLY-LYS-ARG-LYS-ARG-SER-GLN-MET-
CTG TCT CCA GCT GCA AAA ACT GGC AAA CGT AAA AGA TCT CAG ATG 140                  145                    150
LEU-PHE-ARG-GLY-ARG-ARG-ALA-SER-GLN-GLU-PRO-SER-GLY-PRO-ILE-
CTG TTT CGT GGT CGC CGT GCT TCT CAG GAA CCG TCT GGT CCA ATC 155                  160                    165
SER-THR-ILE-ASN-PRO-SER-PRO-PRO-SER-LYS-GLU-SER-HIS-LYS-SER-
TCT ACT ATC AAC CCG TCT CCT CCG TCT AAA GAA TCT CAT AAA TCT 170                  175                    180
PRO-MET-SER-TYR-ASN-LEU-LEU-GLY-PHE-LEU-GLN-ARG-SER-SER-ASN-
CCA ATG AGC TAC AAC TTG CTT GGA TTC CTA CAA AGA AGC AGC AAT 185                  190                    195
PHE-GLN-CYS-GLN-LYS-LEU-LEU-TRP-GLN-LEU-ASN-GLY-ARG-LEU-GLU-
TTT CAG TGT CAG AAG CTT CTG TGG CAA TTG AAT GGG AGG CTT GAA
```

FIG. 9

CHART 3  IFNX 601 (cont.)

```
                200                     205                     210
TYR-CYS-LEU-LYS-ASP-ARG-HIS-ASP-PHE-GLY-PHE-PRO-GLN-GLU-GLU-
TAT TGC CTC AAG GAC AGG CAC GAC TTC GGC TTC CCT CAG GAA GAA 215                     220                     225
PHE-ASP-GLY-ASN-GLN-PHE-GLN-LYS-GLU-ASP-ALA-ALA-LEU-THR-ILE-
TTC GAT GGC AAT CAG TTT CAG AAA GAG GAC GCC GCA TTG ACC ATC 230                     235                     240
TYR-GLU-MET-LEU-GLN-ASN-ILE-PHE-ALA-ILE-PHE-ARG-GLN-ASP-SER-
TAT GAG ATG CTC CAG AAC ATC TTT GCT ATT TTC AGA CAA GAT TCC 245                     250                     255
SER-SER-THR-GLY-TRP-ASN-GLU-THR-ILE-VAL-GLU-ASN-LEU-LEU-ALA-
TCG AGC ACT GGC TGG AAT GAG ACT ATT GTT GAG AAC CTC CTG GCT 260                     265                     270
ASN-VAL-TYR-HIS-GLN-ILE-ASN-HIS-LEU-LYS-THR-VAL-LEU-GLU-GLU-
AAT GTC TAT CAT CAG ATA AAC CAT CTG AAG ACA GTC CTG GAA GAA 275                     280                     285
LYS-LEU-GLU-LYS-GLU-ASP-PHE-THR-ARG-GLY-LYS-LEU-MET-SER-SER-
AAA CTG GAG AAA GAA GAT TTC ACC AGG GGA AAA CTC ATG AGC AGT 290                     295                     300
LEU-HIS-LEU-LYS-ARG-TYR-TYR-GLY-ARG-ILE-LEU-HIS-TYR-LEU-LYS-
CTG CAC CTG AAA AGA TAT TAT GGG AGG ATT CTG CAT TAC CTG AAG 305                     310                     315
ALA-LYS-GLU-TYR-SER-HIS-CYS-ALA-TRP-THR-ILE-VAL-ARG-VAL-GLU-
GCC AAG GAG TAC AGT CAC TGT GCC TGG ACC ATA GTC AGA GTG GAA 320                     325                     330
ILE-LEU-ARG-ASN-PHE-TYR-PHE-ILE-ASN-ARG-LEU-THR-GLY-TYR-LEU-
ATC CTA AGG AAC TTT TAC TTC ATT AAC AGA CTT ACA GGT TAC CTC

ARG-ASN-***-
CGA AAC TGA
```

FIG. 10

CHART 4 IFNX 602

```
              5                              10                             15
MET-GLN-ASP-PRO-TYR-VAL-LYS-GLU-ALA-GLU-ASN-LEU-LYS-LYS-TYR-
ATG CAG GAT CCA TAC GTT AAA GAA GCT GAA AAC CTG AAA AAA TAC 20                             25                             30
PHE-ASN-ALA-GLY-HIS-SER-ASP-VAL-ALA-ASP-ASN-GLY-THR-LEU-PHE-
TTC AAC GCA GGT CAC TCT GAC GTA GCA GAC AAC GGT ACC CTG TTC 35                             40                             45
LEU-GLY-ILE-LEU-LYS-ASN-TRP-LYS-GLU-GLU-SER-ASP-ARG-LYS-ILE-
CTC GGT ATC CTG AAA AAC TGG AAA GAA GAA AGC GAT CGT AAA ATC 50                             55                             60
MET-GLN-SER-GLN-ILE-VAL-SER-PHE-TYR-PHE-LYS-LEU-PHE-LYS-ASN-
ATG CAG TCT CAG ATC GTA TCT TTC TAC TTC AAG CTG TTC AAA AAC 65                             70                             75
PHE-LYS-ASP-ASP-GLN-SER-ILE-GLN-LYS-SER-VAL-GLU-THR-ILE-LYS-
TTC AAA GAT GAT CAG TCG ATC CAA AAA TCC GTT GAA ACT ATC AAA 80                             85                             90
GLU-ASP-MET-ASN-VAL-LYS-PHE-PHE-ASN-SER-ASN-LYS-LYS-LYS-ARG-
GAA GAC ATG AAC GTA AAA TTC TTC AAC TCT AAC AAA AAG AAG CGC 95                            100                            105
ASP-ASP-PHE-GLU-LYS-LEU-THR-ASN-TYR-SER-VAL-THR-ASP-LEU-ASN-
GAT GAC TTT GAA AAA CTG ACT AAC TAC TCG GTG ACC GAC CTG AAC 110                            115                            120
VAL-GLN-ARG-LYS-ALA-ILE-HIS-GLU-LEU-ILE-GLN-VAL-MET-ALA-GLU-
GTA CAG CGT AAA GCT ATC CAC GAG CTC ATT CAG GTT ATG GCA GAA 125                            130                            135
LEU-SER-PRO-ALA-ALA-LYS-THR-GLY-LYS-ARG-LYS-ARG-SER-GLN-MET-
CTG TCT CCA GCT GCA AAA ACT GGC AAA CGT AAA AGA TCT CAG ATG 140                            145                            150
LEU-PHE-ARG-GLY-ARG-ARG-ALA-SER-GLN-ALA-GLY-SER-ALA-GLY-SER-
CTG TTT CGT GGT CGC CGT GCT TCT CAG GCA GGT TCT GCA GGC TCC 155                            160                            165
ALA-GLY-SER-ALA-GLY-SER-ALA-GLY-SER-ALA-GLY-SER-ALA-GLY-SER-
GCT GGC TCC GCA GGT TCC GCT GGT TCT GCC GGC TCT GCA GGC TCT 170                            175                            180
MET-SER-TYR-ASN-LEU-LEU-GLY-PHE-LEU-GLN-ARG-SER-SER-ASN-PHE-
ATG AGC TAC AAC TTG CTT GGA TTC CTA CAA AGA AGC AGC AAT TTT 185                            190                            195
GLN-CYS-GLN-LYS-LEU-LEU-TRP-GLN-LEU-ASN-GLY-ARG-LEU-GLU-TYR-
CAG TGT CAG AAG CTT CTG TGG CAA TTG AAT GGG AGG CTT GAA TAT
```

FIG. II

CHART 4  IFNX 602 (cont.)

```
             200                 205                      210
CYS-LEU-LYS-ASP-ARG-HIS-ASP-PHE-GLY-PHE-PRO-GLN-GLU-GLU-PHE-
TGC CTC AAG GAC AGG CAC GAC TTC GGC TTC CCT CAG GAA GAA TTC 215                 220                      225
ASP-GLY-ASN-GLN-PHE-GLN-LYS-GLU-ASP-ALA-ALA-LEU-THR-ILE-TYR-
GAT GGC AAT CAG TTT CAG AAA GAG GAC GCC GCA TTG ACC ATC TAT 230                 235                      240
GLU-MET-LEU-GLN-ASN-ILE-PHE-ALA-ILE-PHE-ARG-GLN-ASP-SER-SER-
GAG ATG CTC CAG AAC ATC TTT GCT ATT TTC AGA CAA GAT TCC TCG 245                 250                      255
SER-THR-GLY-TRP-ASN-GLU-THR-ILE-VAL-GLU-ASN-LEU-LEU-ALA-ASN-
AGC ACT GGC TGG AAT GAG ACT ATT GTT GAG AAC CTC CTG GCT AAT 260                 265                      270
VAL-TYR-HIS-GLN-ILE-ASN-HIS-LEU-LYS-THR-VAL-LEU-GLU-GLU-LYS
GTC TAT CAT CAG ATA AAC CAT CTG AAG ACA GTC CTG GAA GAA AAA 275                 280                      285
LEU-GLU-LYS-GLU-ASP-PHE-THR-ARG-GLY-LYS-LEU-MET-SER-SER-LEU-
CTG GAG AAA GAA GAT TTC ACC AGG GGA AAA CTC ATG AGC AGT CTG 290                 295                      300
HIS-LEU-LYS-ARG-TYR-TYR-GLY-ARG-ILE-LEU-HIS-TYR-LEU-LYS-ALA-
CAC CTG AAA AGA TAT TAT GGG AGG ATT CTG CAT TAC CTG AAG GCC 305                 310                      315
LYS-GLU-TYR-SER-HIS-CYS-ALA-TRP-THR-ILE-VAL-ARG-VAL-GLU-ILE-
AAG GAG TAC AGT CAC TGT GCC TGG ACC ATA GTC AGA GTG GAA ATC 320                 325                      330
LEU-ARG-ASN-PHE-TYR-PHE-ILE-ASN-ARG-LEU-THR-GLY-TYR-LEU-ARG-
CTA AGG AAC TTT TAC TTC ATT AAC AGA CTT ACA GGT TAC CTC CGA

ASN-***-
AAC TGA
```

FIG. 12

CHART 5 IFNX 603

```
                  5                      10                       15
MET-GLN-ASP-PRO-TYR-VAL-LYS-GLU-ALA-GLU-ASN-LEU-LYS-LYS-TYR-
ATG CAG GAT CCA TAC GTT AAA GAA GCT GAA AAC CTG AAA AAA TAC 20                      25                       30
PHE-ASN-ALA-GLY-HIS-SER-ASP-VAL-ALA-ASP-ASN-GLY-THR-LEU-PHE-
TTC AAC GCA GGT CAC TCT GAC GTA GCA GAC AAC GGT ACC CTG TTC 35                      40                       45
LEU-GLY-ILE-LEU-LYS-ASN-TRP-LYS-GLU-GLU-SER-ASP-ARG-LYS-ILE-
CTC GGT ATC CTG AAA AAC TGG AAA GAA GAA AGC GAT CGT AAA ATC 50                      55                       60
MET-GLN-SER-GLN-ILE-VAL-SER-PHE-TYR-PHE-LYS-LEU-PHE-LYS-ASN-
ATG CAG TCT CAG ATC GTA TCT TTC TAC TTC AAG CTG TTC AAA AAC 65                      70                       75
PHE-LYS-ASP-ASP-GLN-SER-ILE-GLN-LYS-SER-VAL-GLU-THR-ILE-LYS-
TTC AAA GAT GAT CAG TCG ATC CAA AAA TCC GTT GAA ACT ATC AAA 80                      85                       90
GLU-ASP-MET-ASN-VAL-LYS-PHE-PHE-ASN-SER-ASN-LYS-LYS-LYS-ARG-
GAA GAC ATG AAC GTA AAA TTC TTC AAC TCT AAC AAA AAG AAG CGC 95                     100                      105
ASP-ASP-PHE-GLU-LYS-LEU-THR-ASN-TYR-SER-VAL-THR-ASP-LEU-ASN-
GAT GAC TTT GAA AAA CTG ACT AAC TAC TCG GTG ACC GAC CTG AAC 110                     115                      120
VAL-GLN-ARG-LYS-ALA-ILE-HIS-GLU-LEU-ILE-GLN-VAL-MET-ALA-GLU-
GTA CAG CGT AAA GCT ATC CAC GAG CTC ATT CAG GTT ATG GCA GAA 125                     130                      135
LEU-SER-PRO-ALA-ALA-LYS-THR-GLY-LYS-ARG-LYS-ARG-SER-GLN-MET-
CTG TCT CCA GCT GCA AAA ACT GGC AAA CGT AAA AGA TCT CAG ATG 140                     145                      150
LEU-PHE-ARG-GLY-ARG-ARG-ALA-SER-GLN-MET-LEU-PRO-GLY-VAL-GLY-
CTG TTT CGT GGT CGC CGT GCT TCT CAG ATG CTT CCA GGA GTA GGT 155                     160                      165
LEU-THR-PRO-SER-ALA-ALA-GLN-THR-ALA-ARG-GLN-HIS-PRO-LYS-MET-
CTT ACA CCA TCA GCT GCC CAG ACT GCT CGT CAG CAT CCG AAG ATG 170                     175                      180
HIS-LEU-ALA-HIS-SER-THR-LEU-LYS-PRO-ALA-ALA-HIS-LEU-ILE-GLY-
CAT CTT GCC CAC AGC ACC CTT AAG CCT GCT GCT CAC CTC ATT GGT 185                     190                      195
ASP-PRO-SER-LYS-GLN-ASN-SER-LEU-LEU-TRP-ARG-ALA-ASN-THR-ASP-
GAC CCC AGC AAG CAS AAC TCA STG CTC TGG CGC GCA AAC ACC GAT
```

FIG. 13

CHART 5 IFNX 603 (cont.)

```
                200                      205                           210
ARG-ALA-PHE-LEU-GLN-ASP-GLY-PHE-SER-LEU-SER-ASN-ASN-SER-LEU-
CGT GCC TTC CTC CAG GAT GGT TTC TCC TTG AGC AAC AAT TCT CTC 215                      220                           225
LEU-VAL-PRO-THR-SER-GLY-ILE-TYR-PHE-VAL-TYR-SER-GLN-VAL-VAL-
CTG GTA CCC ACC AGT GGC ATC TAC TTC GTC TAC TCC CAG GTG GTC 230                      235                           240
PHE-SER-GLY-LYS-ALA-TYR-SER-PRO-LYS-ALA-THR-SER-SER-PRO-LEU-
TTC TCT GGG AAG GCC TAC TCT CCC AAG GCC ACC TCC TCC CCA CTC 245                      250                           255
TYR-LEU-ALA-HIS-GLU-VAL-GLN-LEU-PHE-SER-SER-GLN-TYR-PRO-PHE-
TAC CTG GCC CAT GAG GTC CAG CTC TTC TCG AGC CAG TAC CCC TTC 260                      265                           270
HIS-VAL-PRO-LEU-LEU-SER-SER-GLN-LYS-MET-VAL-TYR-PRO-GLY-LEU-
CAT GTG CCT CTC CTC AGC TCC CAG AAG ATG GTG TAT CCC GGG CTG 275                      280                           285
GLN-GLU-PRO-TRP-LEU-HIS-SER-MET-TYR-HIS-GLY-ALA-ALA-PHE-GLN-
CAG GAA CCC TGG CTG CAC TCG ATG TAC CAT GGG GCT GCG TTC CAG 290                      295                           300
LEU-THR-GLN-GLY-ASP-GLN-LEU-SER-THR-HIS-THR-ASP-GLY-ILE-PRO-
CTC ACC CAG GGA GAC CAG CTA TCC ACC CAC ACA GAT GGC ATC CCC 305                      310                           315
HIS-LEU-VAL-LEU-SER-PRO-SER-THR-VAL-PHE-PHE-GLY-ALA-PHE-ALA-
CAC CTA GTC CTC AGC CCT AGT ACT GTC TTC TTT GGA GCC TTC GCT

LEU-***-
CTG TAG
```

CHART 6 IFNX 604  FIG. 14

```
                 5                      10                     15
MET-GLN-ASP-PRO-TYR-VAL-LYS-GLU-ALA-GLU-ASN-LEU-LYS-LYS-TYR-
ATG CAG GAT CCA TAC GTT AAA GAA GCT GAA AAC CTG AAA AAA TAC 20                      25                     30
PHE-ASN-ALA-GLY-HIS-SER-ASP-VAL-ALA-ASP-ASN-GLY-THR-LEU-PHE-
TTC AAC GCA GGT CAC TCT GAC GTA GCA GAC AAC GGT ACC CTG TTC 35                      40                     45
LEU-GLY-ILE-LEU-LYS-ASN-TRP-LYS-GLU-GLU-SER-ASP-ARG-LYS-ILE-
CTC GGT ATC CTG AAA AAC TGG AAA GAA GAA AGC GAT CGT AAA ATC 50                      55                     60
MET-GLN-SER-GLN-ILE-VAL-SER-PHE-TYR-PHE-LYS-LEU-PHE-LYS-ASN-
ATG CAG TCT CAG ATC GTA TCT TTC TAC TTC AAG CTG TTC AAA AAC 65                      70                     75
PHE-LYS-ASP-ASP-GLN-SER-ILE-GLN-LYS-SER-VAL-GLU-THR-ILE-LYS-
TTC AAA GAT GAT CAG TCG ATC CAA AAA TCC GTT GAA ACT ATC AAA 80                      85                     90
GLU-ASP-MET-ASN-VAL-LYS-PHE-PHE-ASN-SER-ASN-LYS-LYS-LYS-ARG-
GAA GAC ATG AAC GTA AAA TTC TTC AAC TCT AAC AAA AAG AAG CGC 95                     100                    105
ASP-ASP-PHE-GLU-LYS-LEU-THR-ASN-TYR-SER-VAL-THR-ASP-LEU-ASN-
GAT GAC TTT GAA AAA CTG ACT AAC TAC TCG GTG ACC GAC CTG AAC 110                     115                    120
VAL-GLN-ARG-LYS-ALA-ILE-HIS-GLU-LEU-ILE-GLN-VAL-MET-ALA-GLU-
GTA CAG CGT AAA GCT ATC CAC GAG CTC ATT CAG GTT ATG GCA GAA 125                     130                    135
LEU-SER-PRO-ALA-ALA-LYS-THR-GLY-LYS-ARG-LYS-ARG-SER-GLN-MET-
CTG TCT CCA GCT GCA AAA ACT GGC AAA CGT AAA AGA TCT CAG ATG 140                     145                    150
LEU-PHE-ARG-GLY-ARG-ARG-ALA-SER-GLN-GLU-PRO-SER-GLY-PRO-ILE-
CTG TTT CGT GGT CGC CGT GCT TCT CAG GAA CCG TCT GGT CCA ATC 155                     160                    165
SER-THR-ILE-ASN-PRO-SER-PRO-PRO-SER-LYS-GLU-SER-HIS-LYS-SER-
TCT ACT ATC AAC CCG TCT CCT CCG TCT AAA GAA TCT CAT AAA TCT 170                     175                    180
PRO-LEU-PRO-GLY-VAL-GLY-LEU-THR-PRO-SER-ALA-ALA-GLN-THR-ALA-
CCA CTT CCA GGA GTA GGT CTT ACA CCA TCA GCT GCC CAG ACT GCT 185                     190                    195
ARG-GLN-HIS-PRO-LYS-MET-HIS-LEU-ALA-HIS-SER-THR-LEU-LYS-PRO-
CGT CAG CAT CCG AAG ATG CAT CTT GCC CAC AGC ACC CTT AAG CCT
```

FIG. 15

CHART 6 IFNX 604 (cont.)

```
                200                     205                         210
ALA-ALA-HIS-LEU-ILE-GLY-ASP-PRO-SER-LYS-GLN-ASN-SER-LEU-LEU-
GCT GCT CAC CTC ATT GGT GAC CCC AGC AAG CAG AAC TCA CTG CTC 215                     220                         225
TRP-ARG-ALA-ASN-THR-ASP-ARG-ALA-PHE-LEU-GLN-ASP-GLY-PHE-SER-
TGG CGC GCA AAC ACC GAT CGT GCC TTC CTC CAG GAT GGT TTC TCC 230                     235                         240
LEU-SER-ASN-ASN-SER-LEU-LEU-VAL-PRO-THR-SER-GLY-ILE-TYR-PHE-
TTG AGC AAC AAT TCT CTC CTG GTA CCC ACC AGT GGC ATC TAC TTC 245                     250                         255
VAL-TYR-SER-GLN-VAL-VAL-PHE-SER-GLY-LYS-ALA-TYR-SER-PRO-LYS-
GTC TAC TCC CAG GTG GTC TTC TCT GGG AAG GCC TAC TCT CCC AAG 260                     265                         270
ALA-THR-SER-SER-PRO-LEU-TYR-LEU-ALA-HIS-GLU-VAL-GLN-LEU-PHE-
GCC ACC TCC TCC CCA CTC TAC CTG GCC CAT GAG GTC CAG CTC TTC 275                     280                         285
SER-SER-GLN-TYR-PRO-PHE-HIS-VAL-PRO-LEU-LEU-SER-SER-GLN-LYS-
TCG AGC CAG TAC CCC TTC CAT GTG CCT CTC CTC AGC TCC CAG AAG 290                     295                         300
MET-VAL-TYR-PRO-GLY-LEU-GLN-GLU-PRO-TRP-LEU-HIS-SER-MET-TYR-
ATG GTG TAT CCC GGG CTG CAG GAA CCC TGG CTG CAC TCG ATG TAC 305                     310                         315
HIS-GLY-ALA-ALA-PHE-GLN-LEU-THR-GLN-GLY-ASP-GLN-LEU-SER-THR-
CAT GGG GCT GCG TTC CAG CTC ACC CAG GGA GAC CAG CTA TCC ACC 320                     325                         330
HIS-THR-ASP-GLY-ILE-PRO-HIS-LEU-VAL-LEU-SER-PRO-SER-THR-VAL-
CAC ACA GAT GGC ATC CCC CAC CTA GTC CTC AGC CCT AGT ACT GTC

335
PHE-PHE-GLY-ALA-PHE-ALA-LEU-***-
TTC TTT GGA GCC TTC GCT CTG TAG
```

FIG. 16

CHART 7

Confirmation that polypeptides cell modulator IFN X601 contained both IFN-β and IFN-γ immunogenic epitopes and correct molecular weight, by immunoprecipitation of 35 S-Methionine labelled E.Coli extracts and analysis by SDS-PAGE (17.5% gel, reduced).

Lane group 1 - IFN γ (X918)

2 - IFN β (X430)

3 - IFN γ/IFN X430 (X601)

Monoclonal antibodies used for immunoidentification were:

a)   Anti-IFNγ (Meloy)

b)   Anti-IFNγ (Celltech)

c)   Anti-IFNβ (Searle)

CHART 7 (cont.)

FIG. 18

CHART 8

Western blotting confirmation of co-identity of IFN-β immunoreactivity with IFN X601 36k dalton protein. Lanes (A) = IFN X430, Lanes (B) = IFN X918 and Lanes (C) IFN X601. Monoclonal anti-IFNβ (Searle) was used for immunoidentification and visualised with iodinated anti-mouse IgG (Fab) followed by autoradiography.

CHART 8 (cont.)

COVALENTLY LINKED POLYPEPTIDE CELL MODULATORS SUCH AS INTERFERON-LYMPHOTOXIN CONJUGATES

This is a continuation of application Ser. No. 06/803,748, filed Dec. 2, 1985, now U.S. Pat. No. 4,935,233.

BACKGROUND OF THE INVENTION

1. Field of the Invention

This invention relates to covalently linked polypeptide cell modulators, each of which acts through a different and specific cell receptor to initiate complementary biological activities. Polypeptide cell modulators include lymphokines, monokines, interferons, polypeptide hormones or cytotoxins as well as modifications and active segments of such peptides. Also described are DNA sequences, plasmids and hosts capable of expressing the linked polypeptide cell modulators.

2. Description of Prior Art

One class of polypeptide cell modulators can be defined whose members exert an antiproliferative effect almost specifically on tumour cells and possess immunomodulatory activity, but lack antiviral activity. Among the members of this class are human lymphotoxin and tumour necrosis factor (Gray, P. W. et. al. Nature 312, 721, 1984; Pennica D. et. al. Nature 312, 724, 1984).

Human lymphotoxin (hLT) is a cytotoxin induced in lymphocytes by a specific antigen or by bacteria or parasites and has a cytotoxic or cytostatic action on a variety of tumour cells in vivo or in vitro. hLT has been implicated to play a role in cell-mediated immunity and its potent anti-tumour effect suggests it may be of value therapeutically (Ruddle, N. H. et. al. Lymphokine Res. 2, 23, 1983).

Another class of lymphokine can be defined whose members induce an antiviral state in responsive cells, and also have antiproliferative and immunomodulating activity. Among the members of this class are leukocyte interferon (IFN-alpha), fibroblast interferon (IFN-beta) and immune interferon (IFN-gamma).

It has been reported that mixtures of type I interferons (IFN-beta or IFN-alpha) and type II interferons (IFN-gamma) are highly synergistic in exerting an antiviral or antiproliferative effect. (Fleishmann, W. R. et. al. Infect. Immun. 26, 248, 1979; Czarniecki, C. W. et. al. J. Virol. 49, 490, 1984).

In mixtures, much lower concentrations of type I and type II interferons can achieve a particular level of response. Several authors have also described IFN-gamma/hLT and IFN-alpha/hLT synergy or related synergies (Lee, S. H. et. al. J. Immunol. 133, 1083, 1984; Stone-wolff, D. S. et. al. J. Exp. Med. 159, 828, 1984; Williams, T. W. Lymphokine Res. 3, 113, 1984), European Patent Application (EPO 107 498), (EPO 128009).

However, in these instances, there was no disclosure of covalent linkage of the two classes of molecules that were synergistic.

Additional patent publications have described the primary amino acid sequences of human IFN-gamma (GB 2 107 718 A), the IFN-gamma (IFN X918) described herein (PCT 83/04053), IFN-alphas (U.S. Pat. No. 4,414,150—Aug. 11, 1983 and IFN-beta (e.g. GB 0689 70B; GB 2098996A). A modified IFN-beta (IFN X430) described herein is identical to human fibroblast IFN-beta except that amino acids 36 to 48 inclusive are replaced with amino acids 34 to 46 inclusive from human IFN-alpha 1 (European Patent Application 85105914.7 and (Taniguchi, T. et. al. Nature 285, 547, 1980).

BRIEF DESCRIPTION OF THE INVENTION

This invention encompasses mixed function proteins formed from covalently linked polypeptide cell modulators, each of which acts through a different and specific cell receptor to initiate complementary biological activities. Novel compounds of this invention are represented by the formula

$$R_1-L-R_2$$

where $R_1$ is a polypeptide cell modulator with one activity, $R_2$ is a polypeptide cell modulator with a different but complementary activity. By complementary activity is meant activity which enhances or changes the response to another cell modulator. The polypeptide cell modulators are either directly bonded to one another or are each bound to a polypeptide linker segment. Thus L represents a chemical bond or a polypeptide linker segment to which both $R_1$ and $R_2$ are bound, most commonly L is a linear peptide to which $R_1$ and $R_2$ are bound by amide bonds linking the carboxy terminus of $R_1$ to the amino terminus of L and the carboxy terminus of L to the amino terminus of $R_2$. The linking group is generally a polypeptide of between 1 and 500 amino acids in length.

The term polypeptide cell modulator encompasses a large variety of peptides which elicit a biological response by binding to a specific binding site on a cell. It is known that mixtures of polypeptide cell modulators such as beta and gamma interferon exhibit a synergistic effect. In this invention the polypeptide cell modulators are bound together to produce the same synergistic effect as a mixture of the polypeptide cell modulators or a further enhanced effect or a different effect with the advantage of a single dosage form.

Compounds of this invention are preferably made by genetic engineering techniques. Thus genetic material (DNA) coding for one polypeptide cell regulator, peptide linker segment and the other polypeptide cell regulator is inserted into a suitable vector which is used to transform bacteria, yeast or mammalian cells. The transformed organism is grown and the protein isolated by standard techniques. The resulting product is therefore a new protein which has two complementary cell regulatory regions joined by a peptide linker segment as shown in the formula $R_1-L-R_2$, wherein $R_1$ and $R_2$ represent polypeptide cell regulator regions and L represents the peptide linker segment.

BRIEF DESCRIPTION OF THE CHARTS, TABLES, AND FIGURES

Table 1 shows the origin and identification of the plasmids used in the construction of polypeptide cell modulators.

Table 2 shows expression and molecular weight data for IFN X601.

Table 3 shows a comparison of the antiviral activity of IFN X601 with that of the parental IFNs.

Table 4 shows a comparison of the antiproliferative activity of IFN X601 on Daudi lymphoblastoid cells and HEp-2 carcinoma cells with that of the parental IFNs.

Table 5 demonstrates synergy between human IFN-gamma and IFN X430.

Table 6 shows the antigenic properties of IFN X601 as judged by enzyme-linked immunoadsorbent assay (ELISA).

Table 7 shows a comparison of the binding to Daudi cell IFN alpha 2 receptors of IFN X601 with that of the parental interferons, IFN X918 and IFN X430.

Table 8 shows the antiviral, antiproliferative and HLA DR inducing activity of IFN X601 eluted from monoclonal antibody affinity columns.

Table 9 shows the antiviral, antiproliferative, HLA DR inducing and ELISA activity of IFN X602 compared with IFN X601.

Table 10 shows the antiviral, antiproliferative, HLA DR inducing and ELISA activity of IFN X603.

FIG. 3 depicting Chart 1A shows the path to construction of the plasmid vector pGC269, which expresses IFN X601. FIG. 4 and FIG. 5 depicting Charts 1Aa and 1Ab show preparation of starting plasmid pAP8.

FIG. 6 depicting Chart 1B shows the path to construction of the plasmid vector pZZ102, which expresses IFN X603.

FIG. 7 depicts Chart 2; Chart 2A shows the ligated DNA duplex coding for the spacer amino acids and used to prepare an intermediate plasmid (pGC262) in the construction of pGC269. Chart 2B shows the DNA duplex coding for (Ala—Gly—Ser)$_7$, an alternative spacer for linking IFN X918 to IFN X430.

FIG. 8 and FIG. 9 depicting Chart 3 shows the complete nucleotide and amino acid sequences of the IFN X601 gene and IFN X601, respectively.

FIG. 10 and FIG. 11 depicting Chart 4 shows the complete nucleotide and amino acid sequences of the IFN X602 gene and IFN X602, respectively.

FIG. 12 and FIG. 13 depicting Chart 5 shows the complete nucleotide and amino acid sequences of the IFN X603 gene and IFN X603, respectively.

FIG. 14 and FIG. 15 depicting Chart 6 shows the complete nucleotide and amino acid sequences of the IFN X604 gene and IFN X604, respectively.

FIG. 16 and FIG. 17 depicting Chart 7 shows SDS-PAGE analysis of immunoprecipitates of $^{35}$S-labelled E. coli extracts made with anti IFN-$\beta$ and anti IFN-$\gamma$ monoclonal antibodies.

FIG. 18 and FIG. 19 depicting Chart 8 shows Western blotting confirmation of co-identity of IFN-$\beta$ immunoreactivity with IFN X601 36 kd protein.

FIG. 1 shows the enhanced antiproliferative activity of IFN X601 and a mixture of IFN X918 and IFN X430 against HEp-2 carcinoma cells.

FIG. 2 shows the activity of IFN X601 in inducing HLA DR expression on human fibroblasts in comparison with the parental IFNs used either individually or as a mixture.

DETAILED DESCRIPTION OF THE INVENTION

Figure 5:
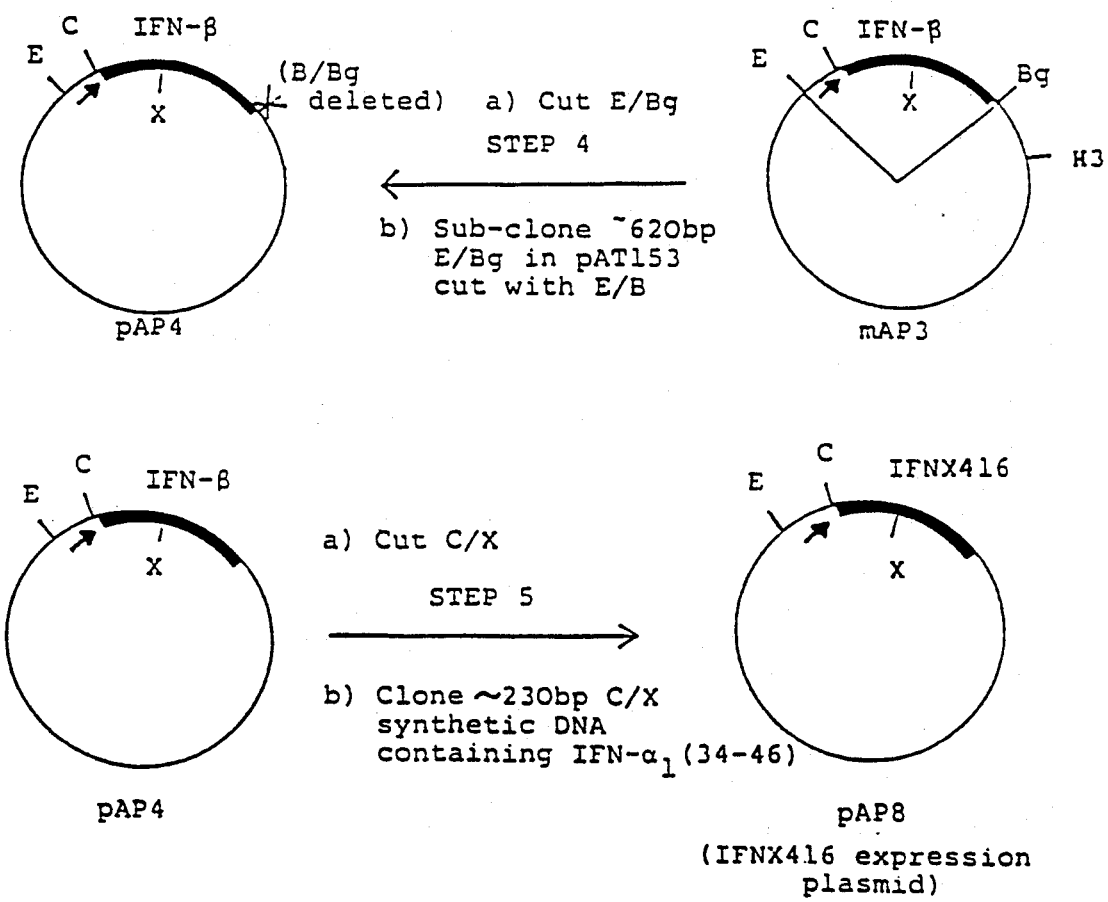

Polypeptide cell modulators include soluble protein modulators released by differentiated cells which have their principle effect on other cell types and include lymphokines, monokines, peptide hormones or peptide growth factors.

Among the polypeptide cell modulators are cytokines, that is, all soluble protein modulators released by a differentiated cell that have their principal effect on other cell types. Included within this cytokine class are lymphokines, monokines, products of the endocrine, paracrine or autocrine hormone systems and polypeptide growth factors.

Specifically included within this cytokine class are the following polypeptides: interleukins 1, 2 and 3, alpha interferons (all types), beta interferon, gamma interferon, lymphotoxin, tumour necrosis factor, epidermal growth factor or urogastrone, B-cell growth factor, insulin like growth factors I and II, bone-derived growth factor, chondrocyte growth factor, T-cell growth factors, endothelial-derived growth factors, nerve growth factor, macrophage-derived growth factor, platelet-derived growth factor, neurotrophic growth factors, transforming growth factor (Type I or II), transforming growth factors, T-cell replacing factor, cartilage-derived growth factor, growth hormone, colony-stimulating factors, insulin, endothelial-cell growth factors, placental lactogen, erthropoietin, plasminogen activators, eye-derived growth factor, prolactin, fibroblast-derived growth factor, relaxin, fibroblast growth factors, thrombin, glial growth factor, transferrin, osteosarcoma-derived growth factor, vasopressin, thymosin, follicle stimulating hormone, luteinizing hormone, thyroid stimulating hormone, calcitonin, adrenal corticotropin, melanocyte stimulating hormone, parathyroid hormone, oxytocin, glucagon, secretin, cholecystokinin, gastrin, angiotensin, angiogenin and the polypeptide releasing factors from the hypothalamus.

Those skilled in the biochemical arts will recognize that modification of the polypeptide cell modulators such as changing amino acid sequences and derived or synthetic portions or regions of active cell modulators are equally useful as polypeptide cell modulators and are included as polypeptide cell modulators.

These polypeptide cell modulators are either linked directly or through a peptide linker segment. The peptide linker segment is generally a polypeptide derived from 1 to 500 amino acids. Other peptide linker segments such as dicarboxylic acids, diaminoalkyls and the like are useful for chemically linking polypeptide cell modulators. Peptide linker segments from the hinge region of heavy chain immunoglobulins IgG, IgA, IgM, IgD or IgE provide an angular relationship between the attached polypeptide cell modulators. Especially useful are those hinge region sections where the cysteines are replaced by serines.

Since the preferred methods for preparing these linked polypeptide cell modulators are through genetic engineering, it is understood that variations in the genetic code can produce polypeptide cell modulators which have the general structure of

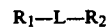

which is a peptide in which $R_1$ and $R_2$ are regions which have sequences which have the above described polypeptide cell modulator activity and L is a peptide linker segment. Large numbers of variations will produce equivalent results. The invention also encompasses glycosylated proteins which for example are produced as a result of expression in yeast or mammalian cells. Also encompassed are variations in the composition of oligasaccharide chains attached to the protein through specific amino acid glycosylation sites. Such variations can be introduced by expression in cells or organisms of varying type of by modification of amino acid glycosylation sites by genetic engineering techniques.

DESCRIPTION OF PREFERRED EMBODIMENTS

Plasmids used in the construction of, or expression of linked polypeptide cell modulator genes are listed in Table 1. One preferred embodiment of the present invention is plasmid pGC269 which codes for IFN X601 (Chart 3) and was derived from plasmids pGC262 (Chart 1A) and pJA39 (Chart 1A). Plasmid pGC262 was derived from plasmid pCC203 (deposited at ATCC no. 39,494) via plasmid pJB9 (Chart 1A); pJA39, which codes for the IFN X430 gene, was derived from plasmid pAP8.

Another preferred embodiment of the present invention is IFN X601 which is composed of sequentially from the N-terminus 1. IFN-gamma in which the N-terminal cys-tyr-cys has been replaced by met (designated IFN X918; Chart 3); 2) a 22 amino acid peptide linker segment coded by synthetic DNA (Chart 2A), related to the mouse IgG 2b "hinge" region (Chart 3, amino acids 145 to 167; and Nature 283, 786, 1980), except that the four cysteines are replaces by serines (Chart 3; serine residues 156, 159, 162 and 166); 3) IFN X430, which is identical to human IFN-beta, except that amino acid residues 36 to 48 inclusive are replaced by the equivalent residues from human IFN-alpha 1 (Chart 3, residues 202 to 214).

The plasmid pGC269 of example 1 below (Chart 1A; Table 1) was used in the expression of a polypeptide cell modulator (IFN X601) of example 2 having the antiviral, antiproliferative and immunomodulatory properties described in example 3.

IFN X918 is just one version of IFN-gamma which may be used (i.e., the N-terminal cys-tyr-cys may be present). IFN X430 is just one example of a type I IFN which may be linked to IFN-gamma, or a modified IFN-gamma, such as IFN X918. Other type I IFNs which may be used include IFN-beta or any IFN-alpha (e.g., IFN-alpha 2; Streuli, M. et al. Science 209, 1343, 1980).

Any suitable peptide linker segment may be used which correctly aligns and separates the two polypeptides comprising the polypeptide cell modulator, for example, the mouse IgG gamma 2b "hinge" region (Nature 283, 786, 1980) with the four cysteines converted to serines (e.g., Chart 3; residues 145 to 167); or a seven times repeated unit coding for alanine-glycine-serine (Chart 2B; and Chart 4; residues 145 to 165) which separates IFN X918 and IFN X430, giving rise to IFN X602 (Chart 4).

A further embodiment is expression plasmid pZZ102 of example 1 which codes for IFN X603 (Chart 5), which was derived from plasmids pZZ101 and pLT101 (Chart 1B and Table 1). Plasmid pZZ101 was derived from plasmid pJB9 by insertion of a 106 bp peptide linker segment coding for the C-terminus of IFN X918 and the amino-terminal 21 amino acids of hLT (Chart 5; residues 132 to 166); plasmid pLT 101 contains a synthetic human lymphotoxin gene (i.e., amino acid residues 146 to 316; Chart 5) cloned between the ClaI and BamHI sites of plasmid pAT153 (Twigg, A. J. Nature 283, 216, 1980). IFN X603 is composed of sequentially from the N-terminus; 1) IFN X918; a single methionine; and 2) human lymphotoxin (Chart 5).

Alternatively, any suitable peptide linker segment may be used which results in significant potentiation of biological activity, but preferably the mouse IgG gamma 2b "hinge" with the four cysteines converted to serines. This modified hinge region may be inserted between IFN X918 and hLT (Chart 6).

It must be appreciated that the DNA sequences coding for IFN X601, IFN X602, IFN X603 and IFN X604 disclosed in charts 3 to 6, are examples of many possible combinations given that alternative triplet codons exist for all amino acids except methionine and tryptophan. Other DNA sequences can code for the amino acid sequences defined in the charts (e.g., Gln-2 in IFN X601 in Chart 3 may be coded by CAG or CAA, etc.).

Expression of polypeptide cell modulators, as in example 2, may be in E. coli K12 HB 101, or other E. coli strain; from any strong promoter and ribosome binding site combination of prokaryotic or eukaryotic origin, but preferably the E. coli strain; from any strong promoter and ribosome binding site combination of prokaryotic or eukaryotic origin, but preferably the E. coli trp promoter minus attenuator (Patent applications EP 130 564 and EP 130 564 A) linked to the following ribosome binding site sequence:

A A G G G T A T C G A T C G A A T G
S.D.                              I.C.

where S.D. is the Shine Dalgarno region and I.C. is the Initiation codon of IFNsX601, or X602, or X603 or X604.

The novel, polypeptide cell modulators of the present invention can be formulated by methods well known for pharmaceutical compositions, wherein the active chimaeron is combined in admixture with a pharmaceutically acceptable carrier substance, the nature of which depends on the particular mode of administration being used. Remington's Pharmaceutical Sciences by E. W. Martin, hereby incorporated by reference, describes compositions and formulations suitable for delivery of the compounds of the present invention. For instance, parenteral formulations are usually injectable fluids that use phsiologically acceptable fluids such as saline, balanced salt solutions, or the like as a vehicle.

The novel, polypeptide cell modulators of the invention may be administered to humans or other animals on whose cells they are effective in various ways such as orally, intravenously, intramuscularly, intraperitoneally, intranasally, intradermally or subcutaneously. Administration of the polypeptide cell modulators is indicated for patients with malignancies or neoplasms, whether or not immunosuppressed, or in patients requiring immunomodulation, or antiviral treatment. Dosage and dose rates may parallel those employed in conventional therapy with naturally occurring interferons—approximately $10^5$ to $10^8$ antiviral units daily. Dosages significantly above or below these levels may be indicated in long term administration or during acute short term treatment. A novel, polypeptide cell modulators may be combined with other treatments or used in association with other chemotherapeutic or chemopreventive agents for providing therapy against the above mentioned diseases and conditions, or other conditions against which it is effective.

EXAMPLE 1

CHEMICAL SYNTHESIS OF OLIGONUCLEOTIDE FRAGMENTS; AND PLASMID CONSTRUCTIONS a) Chemical Synthesis of Oligonucleotides Oligodeoxyribonucleotides were synthesized by the phosphoramidite method (M. H. Caruthers, in "Chemical and Enzymatic Synthesis of Gene Fragments", ed. H. G. Gasen and A. Lang, Verlag chemie, 1982, p. 71) on controlled pore glass (H. Koster et al., Tetrahedron, 1984, 40, 103). Fully protected 2'-deoxyribonucleotide 3'-phosphoramidites were synthesized from the protected deoxyribonucleotide and chloro-N, N-(diisopropylamino) methoxyphosphine (L. J. McBride and M. H. Caruthers, Tetrahedron Lett., 1983, 24, 245 and S. A. Adams et al., J. Amer. Chem. Soc., 1983, 105, 661). Controlled pore glass supports were synthesized as described (F. Chow et al., Nuc. Acids Res., 1981, 9, 2807) giving 30–50 umol deoxynucleoside per gram.

After completion of the synthesis, the protecting groups were removed and the oligomer cleaved from the support by sequential treatment with 3% (v/v) dichloroacetic acid/dichloromethane (120s), thiophenol/triethylamine/dioxane 1/1/2$^v$/v) (1 hour) and concentrated ammonia at 70° C. (4 hour). The deprotected oligonucleotides were purified either by HPLC on a Partisil$^R$ 10 SAX column using a gradient from 1M to 4M triethylammonium acetate pH4.9 at 50° C. or by electrophoresis on a denaturing 15% polyacrylamide gel (pH8.3).

b) Ligation of Oligonucleotide Blocks 500 pmole aliquots of the oligonucleotides were phosphorylated with 1 unit of T4 induced polynucleotide kinase in 20 ul of a solution containing 1000 pmole [$^{32}$p]gamma-ATP (2.5 Ci/mMole), 100 uM spermidine, 20 mM DTT, 10 mM MgCl$_2$, 50 mM Tris-HCl (pH9.0) and 0.1 mM EDTA for 60 minutes at 37° C. The mixtures were then lyophilized and each oligonucleotide purified in a denaturing 15% polyacrylamide gel (pH8.3). After elution from the gel, the recovery was determined by counting the radioactivity.

Blocks (length 30–50 bases were assembled by combining 25 pmole of each phosphorylated component with equimolar amounts of the unphosphorylated oligomers from the complementary strand. The mixtures were lyophilized and then taken up in 15 ul water and 2 ul 10× ligase buffer (500 mM Tris-HCl pH7.6, 100 mM mgCl$_2$). The blocks were annealed at 90° C. for 2 minutes, then slowly cooled to room temperature (20° C.). 2 ul 200 mM DTT and 0.5 ul 10 mM ATP were added to give final concentrations of 20 mM DTT and 250 uM ATP in 10 ul. 1.25 units of T4 DNA ligase were also added. After 18 hours at 20° C., the products were purified in a 15% polyacrylamide gel under denaturing conditions.

The final duplexes were then constructed from the single-stranded pieces. 1.5 pmole of each piece was taken and the mixtures lyophilized. Annealing was carried out in 15 ul water and 2 ul 10× ligase buffer at 100° C. for 2 minutes, then slowly cooled to 10° C. 2 ul 200 mM DTT, 0.5 ul 10 mM ATP and 1.25 units T4 DNA ligase were added. The reaction was left at 10° C. for 18 hours. The final products were then purified in a 10% native polyacrylamide gel.

c) Plasmid Constructions (i) Plasmid pGC269 (Table 1)

STEP 1

DNA corresponding to the amino-terminal cys-tyr-cys of human IFN-gamma in the plasmid pCC203 (ATCC No. 39, 494) was deleted by ClaI/BamHI double restriction enzyme digestion as in Chart 1A (Methods in Molecular Cloning, a Laboratory manual, eds. Maniatis et al., Cold Spring Harbor Laboratory, 1982).

The resultant expression plasmid, pJB9, codes for IFN X918 which has the cys-tyr-cys replaced by methionine (PCT No. 83/04053).

STEP 2

A 171 bp chemically synthesized duplex (Chart 2A) coding for the C-terminal 13 amino acids of IFN X918, 22 amino acids of the mouse immunoglobulin gamma 2b "hinge" region (cys- ser) and 20 N-terminal amino acids of IFN X430, was ligated to the BglII to SalI large vector fragment of pJB9 (Chart 1A). The resultant plasmid, pGC 262 (table 1) contains a HindIII site for insertion of the remainder of the IFN X430 gene.

STEP 3

To create an IFN X416 gene (European Patent application No. 85105914.7) with a unique HindIII site, plasmid pAP8 was cut with ClaI and XhoI (chart IA), and the 230 bp fragment replaced by an identical chemically synthesized fragment except that codons 19 and 20 are AAGCTT (HindIII) instead of AAGCTC. The resultant plasmid was designated pJA39 (Table 1).

STEP 4

Since IFN X416 and IFN X430 are identical except at amino acid position 17, the HindIII to SalI 719 bp fragment from pJA39 (equivalent to amino acids 19 to 166 of IFN X430 or IFN X416) was ligated to the large HindIII/SalI vector fragment of pGC262 to give plasmid pGC269, which codes for the IFN X918 - IFN X430 polypeptide cell modulator, designated IFN X601 (Chart 3).

(ii) Plasmid pZZ102 (Table 1)

A similar strategy was used to construct pZZ102.

STEP 1

Plasmid pJB9 (Chart 1B) was cut with BglII and SalI and a 106 bp chemically synthesized duplex, coding for the C-terminal 13 amino acids of IFN X918 (as in Chart 2A); and a single methionine followed by the 21 N-terminal amino acids of human lymphotoxin (Chart 5; residues 132 to 166) was ligated to the BglII to SalI large vector fragment of pJB9 (Chart 1B). The resultant plasmid, pZZ101, contains an NsiI site at hLT condons 20 and 21 (Gray, P. W. et al. Nature 312, 721, 1984) for insertion of the remainder of the hLT gene, i.e.

STEP 2

Plasmid pZZ101 was cleaved with NsiI and SalI and the large vector fragment isolated in preparation for insertion of the remainder of the hLT gene, which was isolated from pLT101 (Table 1; chart 1B).

pLT101 contains a complete synthetic hLT gene modified from Gray, P. W. et al. Nature 312, 721, 1984 (equivalent to amino acid residues 145 to 316 in Chart 5). The hLT gene in pLT 101 was cloned on a ClaI to BamHI fragment in the ClaI/BamHI sites of plasmid pAT153. The nucleotide sequences of the ClaI and BamHI junctions are, respectively: A T C G A T A A G C T A T G. and T A G A G G A T C C (ATG-=initiation codon, TAG=termination codon).

Plasmid pLT101 was cleaved with NsiI and SalI and the resultant 725 bp small fragment was ligated to the NsiI and SalI large vector fragment of ppZZ101 (Chart 1B) to give plasmid pZZ102, which codes for the IFN X918-lymphotoxin polypeptide cell modulator, designated IFN X603 (Chart 5).

EXAMPLE 2

EXPRESSION AND ISOLATION OF POLYPEPTIDE CELL MODULATORS a) Expression of plasmids coding for IFN X601, X602, X603 and X604

Overnight cultures (10 ml.) of transformed bacteria were grown in M9/casamino acids medium (EP 131 816A) supplemented with tryptophan (40 ug/ml) and ampicillin (100 ug/ml). Inocula (0.5 ml.) were added to 50 ml. M9/casamino acids medium containing 100 ug/ml. ampicillin. Growth was continued at 37° C. until the A 670 nm had reached 0.5, at which time the cultures were made 20 ug/ml. with respect to beta -indole acrylic acid in order to induce the synthesis of polypeptide cell modulators. Growth was at 37° C. with vigorous shaking, and samples for biological assay (as described in example 3 below) and electrophoretic analysis were removed at 4 hours after induction.

b) SDS-polyacrylamide gel electrophoresis of total *E. coli* proteins for estimation of expressed protein content The volume of cells equivalent to 0.5 optical density units at 670 nm was removed from the culture immediately and at 4 hours after adding IAA, and the bacteria recovered by centrifugation. The cells were immediately resuspended in 50 ul of 60 mM tris-HCl pH6.8, 0.05% bromophenol blue, 5% glycerol, 1% sodium dodecylsulphate, 0.5% 2-mercaptoethanol, heated at 100° C. for 3 min. and quick frozen on dry ice. The boiling-freezing cycles were repeated 2-3 times to reduce the viscosity of the sample before a final boiling 5 minutes prior to loading 7.5 $\mu$l on a 15% SDS- polyacrylamide gel (Molecular Cloning, A Laboratory Manual, ibid.). The gel was stained with coomassie brilliant blue and dried. The dried gel was scanned with a Joyce-Loebl 'chromascan 3' gel scanner, which computes the percentage of total protein for each polypeptide band.

Results

Table 2 shows that for IFN X601, a polypeptide of approximately the size expected for an IFN X918/hinge/IFN X430 fusion is expressed in the range 5.4 to 10% of total bacterial protein.

This polypeptide is absent from cultures of *E. coli* K12 HB 101 harbouring plasmid pJB9 expressing IFN X918 ($\sim$17K) or pIL201 expression IFN X430 ($\sim$19K).

c) Preparation of bacterial extracts for biological assay 10 to 20 ml. of bacterial culture was removed at the optical density (670 nm) of 1.5-2.0 (middle to late log phase of growth) and centrifuged to recover the cells. After suspension in 25 mM tris-HClpH 7.5, 50 mM NaCl (1 ml.) and 1 mM EDTA (1.4 ml.) at 0° C., 28 ul lysozyme was added to a final concentration of 50 ug/ml and the suspension incubated at 0° C. for 30 min. The suspension was sonicated for 24 sec., the cell debris removed by centrifugation and the supernatants assayed for biological activity as described in Example 3 or gel analysis as described in Example 2.

Alternatively, lysis without sonication was used as follows. 10 ml. of bacterial culture was centrifuged and the bacterial pellet resuspended in 2 ml. 30 mM NaCl, 50 mM tris-HCl pH 7.5, 0.05 to 1 mg/ml lysozyme. Following incubation at 25° C. for 10 min. and 0° C. for 15-30 min. three freeze-thaw cycles were performed ($-70°$ C.). The supernatant from a 15,000 rpm, 15 min. centrifugation was divided for gel analysis, protein estimation and assay.

EXAMPLE 3

BIOLOGICAL ACTIVITY OF POLYPEPTIDE CELL MODULATORS IN CRUDE BACTERIAL EXTRACTS a) Antiviral assay The cellular extract prepared as in Example 2 (together with 1 log dilutions to $10^{-6}$) was assayed for antiviral activity by monitoring the protection conferred on Vero (African Green Monkey) cells against the cytopathic effect of encephalomyocarditis (EMC) virus infection in an in vitro microplate assay system; for example, Dahl, H. and Degre, M. Acta. Path. Microbiol. Scan., 1380, 863, 1972.

Results

A comparison is made in Table 3 of the antiviral (AV) activity in crude bacterial extracts of IFN X601 and the parental IFNs, derived from equivalent numbers of bacterial cells. IFN X601 consistently exhibited 2.5-3.0 fold higher AV activity than IFN X430 and a 4-6 fold higher AV activity than IFN X918, despite a $\sim$2- fold lower level of protein expression (Table 2).

A 1:1 mixture of the separately expressed IFNs X918 and X430 also exhibited a significantly enhanced AV activity, which was 4 fold higher than the value expected if the AV activities of the individual IFNs X918 and X430 were additive (Table 3). This is a reflection of the known synergy between Type I and Type II IFNs (Czarniecki, C. W. et al. J. Virol. 49, 490, 1985; and EP 0107 498).

In conclusion, the polypeptide cell modulator IFN X601 displayed a significant enhancement of AV activity compared with the parental IFNs, which was similar to that of equimolar mixtures of IFN X918 and IFN X430.

b) Antiproliferative assays (i) Daudi (lymphoblastoid) cells

Antiproliferative (AP) activity was assessed by the ability of the polypeptide cell modulator to inhibit the replication of Daudi (lymphoblastoid) cells (Horoszewicz et al. Science 206, 1091, 1979). Daudi cells in log phase were cultured for 6 days in 96 well plates in the presence of various dilutions of chimaeron or IFN. The phenol red in the medium changes from red to yellow (more acid) with progressive cell growth. Liquid paraffin was added to prevent pH change on exposure to the atmosphere, and the pH change in the medium measured colorimetrically on a Dynatech plate reader. Inhibition of cell growth is reflected by a corresponding reduction in the colour change.

Results

A comparison is made in Table 4A of the Daudi lymphoblastoid cell antiproliferative activity in crude bacterial extracts of IFN X601 and the parental IFNs derived from equivalent numbers of bacterial cells. Daudi cells are known to be unresponsive to IFN-gamma and in a similar fashion did not respond to the antiproliferative action of IFN X918, being more than 100X less sensitive to IFN X918 than to IFN X430 (Table 4A). By contrast, IFN X601 exhibited similar activity to that of IFN X430. Mixtures of IFN X918 and IFN X430 gave a lower titre than with IFN X430 alone i.e., synergy was not evident. These results are expected as the Daudi cell line is capable of responding to the antiproliferative effect of only the IFN X430 portion of the polypeptide cell modulator. These results also indicate that the IFN X430 portion of the polypeptide cell modulator functionally active, contributing to its biological activity (Tables 3 and 4B).

Consistent with these findings is the observation that there is a similar level of binding of IFN X430 and IFN X601 to Daudi receptors (Table 7), while the lack of AP activity of IFN X918 correlates with very low receptor binding.

(ii) HEp-2 (human laryngeal carcinoma) cells

Antiproliferative activity was also assessed in HEp-2 cells Growth inhibition was measured by methylene blue staining of the cell monolayer by a modification of the method of Ito. (Ito, M. J. Interferon Res. 4, 603, 1984). Inhibitory concentration ($IC_{50}$) end point is the log dilution giving 50% reduction of methylene blue staining.

Results

A comparison is made in Table 4B of the HEp-2 antiproliferative activity in crude bacterial extracts of IFN X601 and the parental IFNs, derived from equivalent numbers of bacterial cells. IFN X601 consistently displayed a 3 fold higher AP activity than IFN X430 and a 15 fold higher AP activity than IFN X918, despite a ~2-fold lower level of protein expression (Table 2). Furthermore, when equivalent antiviral units of these interferons were compared it was seen that IFN X601 had an enhanced antiproliferative effect as shown in FIG. 1. For the individual IFNs X430 and X918 there is a maximum achievable level of growth inhibition which cannot be increased despite adding a hundredfold excess of interferon. This is not seen with IFN X601 where a markedly increased level of growth inhibition is seen.

These properties of IFN X601 are reminiscent of the antiproliferative effect of mixtures of IFN X430 and IFN X918. For example, Table 4B shows the equivalent concentrations of these two IFNs mixed together gave 1.8-8.6 fold higher AP activity than either alone. In this case, AP activity was almost 3 fold higher than the value expected if the AP activities of the individual IFNs X918 and X430 were additive (Table 4B). Further, like IFN X601, equimolar mixtures of IFN X918 and IFN X430 have enhanced antiproliferative activity against HEp-2 cells (FIG. 1).

Potentiation of AP activity by mixtures of IFN X918 and IFN X430 is a reflection of the synergy which can be demonstrated between IFN-gamma (equivalent to IFN X918) and IFN X430 and is illustrated by the results presented in Table 5. Where the FIC index (as defined in Table 5) is less than 0.5, synergy is evident. Maximum synergy was observed at equivalent numbers of antiviral units of IFN-gamma and IFN X430 (10 U/ml). Since the specific activities of IFN-gamma and IFN X430 differ only by a factor of approximately two, similar amounts of IFN protein are also present.

Taken together, these results indicate that (i) a covalent combination of IFN X918 and IFN X430 via a peptide linker segment potentiates cytotoxicity in a manner analogous to simple mixtures; (ii) a covalent combination of IFN X918 and IFN X430 is a suitable ratio to potentiate biological activity; (iii) the $IC_{50}$ end point on HEp-2 cells for IFN X601 was significantly higher than the values for the parental IFNs. Potentiation was similar to that observed with synergistic mixtures of IFN X918 and IFN X430.

c) HLA-DR Antigen presentation on human fibroblasts

IFN-gamma, but not IFN-beta or IFN X430, induces the expression on the surface of normally DR-negative human foetal lung fibroblasts (17/1 strain). This is detected and measured by the binding of monoclonal antibody against HLA-DR.

Fibroblasts are grown to confluence in DMEM/10% FCS (Dulbecco's Modified Eagles Medium) in 96-well tissue culture plates. IFN-gamma or modified IFN is serially diluted in DMEM/0.1% BSA and dilutions are added to the medium on the fibroblasts. The fibroblasts are incubated at 37° C. for a further 3 days and then the medium is removed and the cells are washed once with PBS. Admixtures in Herpes-buffered DMEM of a monoclonal antibody directed against HLA-DR and peroxidase conjugated antibody against mouse IgG, is added to the cells and incubated at room temperature for 2 hours. The cells are washed five times with PBS and then the amount of anti-DR antibody bound to the cells is measured by assaying for bound peroxidase using tetramethyl benzidine (TMB) as a chromogen. The colour generated is measured with a Dynatech TM microelisa reader.

Results

IFN X601 and IFN X918 clearly caused expression of HLA-DR antigens on the surface of 17/1 fibroblasts while IFN X430 did not (table 9). The level of HLA DR induction by IFN X601 was markedly lower than that induced by equivalent antiviral units of IFN X918. This may be due to suppression by the IFN X430 domain because the HLA DR induction by IFN X918 was seen to be reduced in a 1:1 mixture with IFN X430. The HLA DR induction by IFN X601 can be increased more than ten fold by blocking the activity of the IFN X430 domain with anti IFN-$\beta$ monoclonal antibody. These results demonstrate that IFN-gamma biological activity is present in the polypeptide cell modulator IFN X601.

d) Analysis of IFN X601 with Antibodies Against beta and gamma -IFNs i) Enzyme linked immunoadsorbent assay (ELISA) for interferon The ELISA for both beta and gamma interferons utilizes an indirect two site sandwich technique. Dilutions of the interferon samples (or standards) are allowed to bind to interferon antibodies attached to the wells of a 96 well microplate. A second antibody to interferon, but raised in a different species from that attached to the plate, is included in the incubation mixture, which then binds to a second epitope on the interferon molecule. After washing away the unbound molecules, an enzyme labelled antispecies antibody is added which binds to the second interferon antibody. The presence of bound enzyme is detected by adding a substrate which changes color in the presence of enzyme. The amount of color produced is proportional to the amount of interferon, since the other reagents are present in excess.

For the beta and gamma interferon ELISA's, two antibodies against the corresponding interferon are used, while for a hybrid ELISA, an antibody directed against beta interferon is bound to the plate, while the second antibody used is one directed against gamma interferon.

The general scheme of the assay is illustrated below:

MICROTITER PLATE

-continued

ANTIBODY TO INTERFERON
INTERFERON SAMPLE
SECOND ANTIBODY TO INTERFERON
ANTI SPECIES ANTIBODY
(ENZYME LABELLED)

BETA INTERFERON ELISA 96 well microplates (Nunc Immunoplate 1) are coated with a goat anti human beta interferon antibody (Rega Institute). To each well of a microplate, is added 100 microliter of a 5 microgram/ml solution of immunoglobulin (obtained by a 40% ammonium sulphate precipitation of the interferon antibody) in 0.05M sodium carbonate buffer, pH 9.8, and incubated for two hours at room temperature. After removal of the well contents, unoccupied binding situes are blocked by incubation with 100 microliters of phosphate buffered saline containing 0.5% casein (PBS/C), for 30 minutes at room temperature. The plates are then washed six times with phosphate buffered saline containing 0.05% Tween 20 (PBS/T), and stored at +4° C. in a covered moist box until required.

Serial dilutions of interferon samples are made in the plates, by dilution in PBS/C containing a mouse monoclonal antibody to beta interferon at a 1/100 dilution. Each plate also contains an internal standard which has been calibrated against the International Reference Standard. After incubation overnight at +4° C., the well contents are removed and the plates washed six times with PBS/T.

100 microliters of peroxidase conjugated goat antimouse immunoglobin (Sigma a7282, diluted 1/2000 in PBS/T), are added to each well and incubated for thirty minutes at room temperature. The well contents are removed and the plates are washed six times with PBS/T. 100 microliters of TMB (Tetramethyl benzidine, Sigma, 50 mcg/ml in 0.1N acetate/citrate buffer pH 6.0, containing 0.0022% hydrogen peroxide) are added and incubated for one hour at room temperature. 25 microliters of 2.5M sulphuric acid is added to stop the reaction and the optical density read at 450 nm in an automatic plate reader (Titertek Multiscan MC). Data is fed into a computer and the 50% end points determined by linear regression analysis of the logic log transformed data. Corrections are then made to the internal standard included on each plate.

GAMMA INTERFERON ELISA

This assay is carried out in the same way as the beta ELISA, with the following changes: the plates are coated with a mouse monoclonal antibody to gamma interferon (Meloy Laboratories) at 1/200 in carbonate buffer. Serial dilutions of the gamma interferon samples are made in PBS/C containing a rabbit antiserum to human gamma interferon (Immunomodulator laboratories, diluted to 1/5000). A peroxidase conjugated goat anti rabbit immunoglobulin (Tago Laboratories, diluted to 1/3000) is used as the indicator molecule.

HYBRID BETA/GAMMA INTERFERON ELISA

The only difference from the beta ELISA is that the interferon samples are diluted in PBS/C containing a mouse monoclonal to human gamma interferon (Meloy Laboratories, at a dilution of 1/1000). This assay will only detect interferon molecules containing both a beta and a gamma epitope.

Results

The results of testing the polypeptide cell modulator IFN X601 and the appropriate controls in the beta, gamma and hybrid ELISA's are given in Table 6. In the beta ELISA, IFN X430 (equivalent to beta) reacts, the gamma interferon shows no sign of cross reactivity, while a 50/50 mixture of the two gives a titre reduced by 0.4 log unit/ml, close to the expected 0.3 reduction. The IFN X601 also reacts strongly, showing that the two beta interferon epitopes are still available to bind antibodies.

In the gamma ELISA, the gamma interferon reacts, the IFN X430 shows no cross reactivity, while a 50/50 mixture of the two gives a titre reduced by the expected 0.3 log units/ml. IFN X601 also reacts, though with a reduced titre compared to the other positive reactions, which might indicate that one of the gamma epitopes is slightly sterically affected by the presence of the beta hybrid interferon.

In the hybrid ELISA, the only sample to react is IFN X601, which conclusively demonstrates that the molecule contains both beta and gamma epitopes covalently bonded to each other. Quantitatively the results from this assay cannot be compared to the other two ELISA's since there is no standard available and the 50% end points are dependent on relative affinities and concentrations of the various reagents used, which differ for the three assays used. However, the results indicate that a substantial proportion of the polypeptide cell modulators is present in the covalently linked state in sample X601.

(ii) Immunoprecipitation

Interferons were labelled by including $^{35}S$-methionine in bacterial growth medium and extracts were prepared by treatment by lysozyme and sonication. $^{35}S$-labelled *E. coli* extracts were immunoprecipitated with either monoclonal antibodies directed against IFN-$\beta$ or IFN-$\gamma$ and the immunoprecipitates were analyzed by SDS-PAGE.

Results

The results in Chart 7 show that anti IFN-$\beta$ monoclonal antibody precipitates IFN X430 but not IFN X918, anti IFN-$\gamma$ monoclonal antibody precipitates IFN X918 but not IFN X430 while both monoclonal antibodies precipitate a ~36 kd protein in the IFN X601 extract. The material precipitated from the IFN X601 extracts by both antibodies therefore has the predicted molecular weight for the chimaeric protein and has both X430 and X918 antigenic activity.

(iii) Western Blot Analysis

Bacterial extracts containing IFNs were run out on SDS-PAGE and analyzed by Western blotting with anti IFN-$\beta$ monoclonal antibody.

Results

Chart 8 shows that anti-IFN-$\beta$ monoclonal antibody detects IFN X430 in lanes A, does not recognize IFN X918 in lanes B and recognizes a ~36 kd band in the IFN X601 extract in lanes C. This again demonstrates that a band in the IFN X601 extract which is recognized by anti-IFN-$\beta$ monoclonal antibody has the predicted MW for the chimaeric protein IFN X601.

(iv) Monoclonal antibody affinity column purification

Bacterial extracts containing IFN X601 were loaded on to monoclonal antibody affinity columns consisting of either anti-IFN-$\beta$ bound to CNBr sepharose or anti- IFN-γ bound to CNBr sepharose (Celltech MAb). The loaded columns were extensively washed, bound material was eluted and fractions were assayed for antiproliferative activity against Daudi and HEp-2 cells and for HLA DR inducing activity on human lung fibroblasts.

Results

The results in Table 8 demonstrate that material from an *E. coli* lysate containing IFN X601 can be bound to and eluted from both anti-IFN-β and anti-IFN-γ affinity columns. The material eluted from the anti-IFN-β column must have IFN X430 antigenicity and has been shown to have IFN X430 biological activity (Daudi antiproliferative assay) as well as IFN X918 activity in the HLA DR induction assay. The material eluted from the anti-IFN-γ column must have IFN X918 antigenicity and has been shown to have IFN X918 biological activity (HLA DR induction activity) as well as IFN X430 activity in the Daudi antiproliferative assay. In addition, eluted material from both columns showed enhanced antiproliferative activity against HEp-2 cells which is taken to indicate that both the IFN X430 and IFN X918 domains are biologically active.

Biological Activity of IFN X602 (IFN X918 (AGS), IFN X430)

Table 9 shows X602 to have similar biological properties as X601.

Biological Activity of IFN X603 (IFN X918-hLT)

Table 10 shows that IFN X603 retains both lymphotoxin and interferon-like activities. Antiproliferative activity against mouse L cells is characteristic of LT activity, while AV, HLA DR and ELISA give characteristic IFN-gamma activities. (HEp-2 antiproliferative activity could be due to IFN-gamma or lymphotoxin-/IFN-gamma combination but not to lymphotoxin alone.)

EXAMPLE 4

CONSTRUCTION OF THE PLASMID pAP8 EXPRESSING IFNX416

Charts 1Aa and 1Ab illustrate the path to constructing a high level expression vector for IFN-β[β(36-48-)→α$_1$(34-46)][cys$^{17}$→ser$^{17}$], also referred to as IFNX416, in the host *E. coli* HB101 (European Patent No. 85105914.7). The starting vector was p1/24C (~4,440 bp) which was identical to plasmid p1/24 U.K Patent 8,102,051, except for the underlined sequences which follows:

Step 1 (Chart 1Aa)

The subcloning of the natural human IFN-β gene from plasmid p1/24C (Taniguchi et al., Gene, 10, 11, 1980) in phage M13mp8 (Sanger, F. et al., J. Mol. Biol., 143, 161, 1981) was performed, and the presence of the whole fragment was confirmed by restriction endonuclease mapping of M13 plasmid mAP2.

Step 2 (Chart 1Aa)

The technique of "site-directed mutagenesis" (Zoller and Smith, Nucl. Acids Res., 10, 6487, 1982) was employed to introduce two base changes, one each in the IFN-β codons 74 and 75 so as not to change the encoded amino acid sequence. Supercoiled DNA resulting from transcription/ligation was separated from nonligated DNA in a 1% agarose gel and used to transform *E. coli* JM101. Total plasmid DNA was prepared.

Step 3 (Chart 1Aa)

Mutant DNA bearing a unique XhoI site was separated from non-mutant DNA by XhoI restriction and electrophoresis in 1% agarose. The linear DNA was electroeluted from the agarose (Molecular cloning, A Laboratory Manual, eds. Maniatis et al., p. 168, Cold Spring Harbor Laboratories). Following self-ligation of the linear DNA and transformation of *E. coli* JM101, M13 clones were obtained all of which had a unique XhoI site, one of which was designated mAP3.

Step 4 (Chart 1Ab)

The complete IFN-β gene with an XhoI site spanning codons 74–76 was recloned back in pAT153. This generated a vector (pAP4) similar to p1/24C, except for the changed codons 74 and 75 and the deletion of the ~546 base pair BglII-BamHI fragment, originally lying 3′ to the IFN-β coding sequence. The new sequence of the Serine codons 74 and 75 is given in Chart 1Aa.

Step 5 (Chart 1Ab)

The ~230 bp synthetic DNA fragment, assembled as described above, was cloned in the ClaI-XhoI sites of plasmid pAP4 to give pAP8 (Chart 1Ab), a plasmid expressing IFNX416 in the host *E. coli* HB101.

Modifications of the above described mode for carrying out the invention such as, without limitation, use of alternative vectors, alternative expression control systems, and alternative host micro-organisms and other therapeutic or related uses of the novel polypeptide cell modulators that are obvious to those of ordinary skill in the biotechnology, pharmaceutical medical and/or related fields are intended to be within the scope of the following claims.

TABLE 1

| Table of Plasmids | | |
|---|---|---|
| Plasmid | Properties | Source |

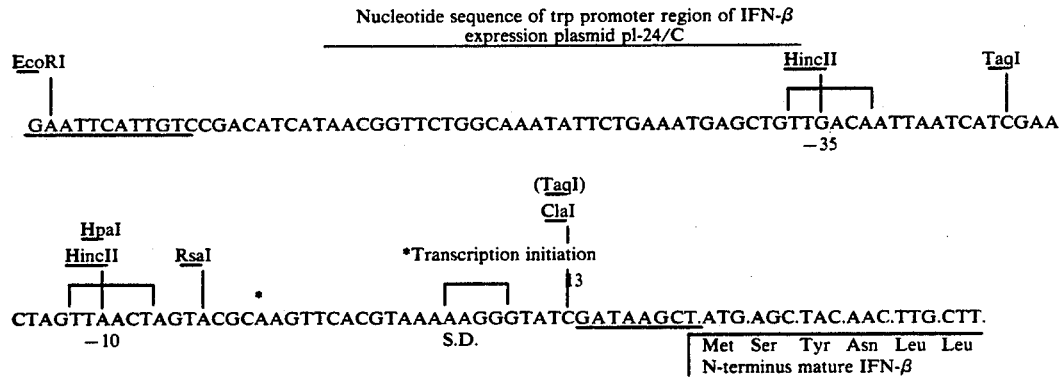

| | | |
|---|---|---|
| pAP8 | Expression vector coding for IFN X416 gene | EP 85105914.7 U.K. Patent 8,102,051, Chart 1Aa and 1Ab |

TABLE 1-continued

Table of Plasmids

| Plasmid | Properties | Source |
|---|---|---|
| pJA39 | Expression vector containing IFN X416 gene plus HindIII site | and example 4 Amino acids 19/20 coded by AAG.CTT instead of AAG.CTC (pAp8) |
| pGC262 | Intermediate vector in construction of pGC269 — codes for IFN-gamma + 22 amino acid mouse gamma 2b IgG "hinge" | Chart 1A |
| pCC203 | Expression vector containing synthetic human IFN-gamma gene | Chart 1A and PCT 83/04053 |
| pJB9 | Expression vector containing synthetic IFN-gamma gene with DNA coding for N-terminal Cys—Tyr—Cys deleted and replaced by Met. (IFN X918) | Chart 1A and PCT 83/04053 |
| LT3/1 | Expression vector containing synthetic human lymphotoxin gene | Charts 1A, 3 Nature 312, 721, 1984 |
| pGC279 | Intermediate vector in construction of pZZ102; codes for IFN X918 plus 22 N-terminal amino acids of lymphotoxin | Chart 1B |
| pZZ102 | Expression vector containing IFN X603 gene (IFN X918 - met-lymphotoxin polypeptide cell modulator). | Charts 1B, 5 |
| pGC269 | Expression vector containing IFN X601 gene. | Charts 1A, 3 |

TABLE 2

Molecular Weight and Expression in *E. coli* of IFN X601

| Interferon | Molecular weight (from polyacrylamide gel) | Range of expression (% of total bacterial protein) |
|---|---|---|
| X918* | 17,000 | 13.6–15.6 (N = 14.6) |
| X430+ | 19,000 | 12.3–17.0 (N = 14.65) |
| X601 | 37,500 | 5.4–10.0 (N = 7.7) |

*IFN-gamma with N-terminal cys—tyr—cys deleted and replaced by met (Chart 3)
+IFN-beta with amino acids 36 to 48 inclusive replaced by amino acids 34 to 46 inclusive from IFN-alpha 1.
N mean.

TABLE 3

Antiviral Activity of IFN X601

| Interferon | Antiviral activity I.U/ml at 10 A670 × $10^{-6}$ | Increase compared with: IFN X430 | Increase compared with: IFN X918 |
|---|---|---|---|
| X918[1] | 0.59 | (0.5X) | — |
| X430 | 1.1 | — | 2.9X |
| X601 | 2.87 | 2.6X | 4.9X |
| X918 + X430[2] | 3.47 | 3.2X | 5.9X |

*IU/ml 10 A670 × $10^{-6}$. Mean of 3 determinations in 2 separate experiments:
1. IFN-gamma with N-terminal Cys—Tyr—Cys replaced by Met (chart 3).
2. Approximately 1:1 mixture of each IFN (protein).

TABLE 4

| Interferon | Antiproliferative Activity* | Increase compared with: IFN X430 | Increase compared with: IFN X918 |
|---|---|---|---|
| A. Daudi lymphoblastoid cells | | | |
| X918 | 0.004 | — | — |
| X430 | 2.7 | — | — |
| X601 | 3.3 | 1.2X | — |
| X918 plus X430[1] | 1.9 | (0.7X) | — |
| B. HEp-2 carcinoma cells | | | |
| X918 | 0.57 | (0.2X) | — |
| X430 | 2.8 | — | 4.9X |
| X601 | 9.0 | 3.2X | 15.8X |
| X918 plus X430[1] | 4.9 | 1.8X | 8.6X |

*Units/ml × $10^{-4}$ = dilution of IFN at 50% cell growth inhibition.
Mean of 2 determinations.
[1] Mixture 1:1 w/w

TABLE 5

IFN X430/IFN-gamma synergy on HEp-2 carcinoma cells

| A. IFN X430 Antiviral Units/ml | FIC* "A" | B. IFN-gamma+ Antiviral units/ml | FIC* "B" | FIC Index ("A" + "B") |
|---|---|---|---|---|
| 168 | 1.000 | 0 | 0.000 | 1.000 |
| 56 | 0.334 | 0.3 | 0.003 | 0.337 |
| 40 | 0.230 | 1.0 | 0.009 | 0.239 |
| 32 | 0.188 | 3.1 | 0.029 | 0.217 |
| 10 | 0.059 | 10 | 0.094 | 0.153 |
| 3.1 | 0.018 | 27 | 0.252 | 0.270 |
| 2.2 | 0.013 | 32 | 0.298 | 0.311 |
| 1.0 | 0.006 | 81 | 0.767 | 0.773 |
| 0.8 | 0.004 | 100 | 0.940 | 0.944 |
| 0 | 0 | 106 | 1.000 | 1.000 |

*FIC. Fractional Inhibitory Concentration - Ratio: antiviral units at 50% cell growth inhibition of a given IFN (e.g. 'A') in combination with another IFN (e.g. 'B') to antiviral units of IFN-'A' alone.
Concentration of IFN alone or in combination required to produce 50% inhibition of HEp-2 growth.
Synergy is present when FIC index is equal to or less than 0.5

TABLE 6

| | ACTIVITY (LOG UNITS/ML) | | | | | |
|---|---|---|---|---|---|---|
| | Beta ELISA | | Gamma ELISA | | Hybrid ELISA | |
| | E | F | E | F | E | F |
| A Gamma interferon | ND | ND | 4.47 | 5.44 | ND | ND |
| B IFN X430 (=beta) | 3.95 | 5.84 | ND | ND | ND | ND |
| C Interferon X601 | 4.13 | 6.02 | 2.98 | 3.95 | 3.73 | — |
| D Mixture of A and B (1:1) | 3.59 | 5.48 | 4.16 | 5.13 | ND | ND |

Notes
1. E represents the 50% end points
2. F represents the corrected activities
3. ND is not detectable activity

TABLE 7

COMPETITION BY IFN X601 FOR THE BINDING OF $^{125}$I-IFN alpha 2 TO DAUDI CELL RECEPTORS

| IFN | Activity Log U/ml.* |
|---|---|
| X430 | 7.0 |
| X918 | 3.6 |
| X601 | 6.6 |

*IFN α2 antiviral unit equivalents.
The activity in each sample was calculated by interpolation from a standard dose curve of the competition by IFN α2 for the binding of $^{125}$I-IFNα2.

TABLE 8

MONOCLONAL ANTIBODY AFFINITY PURIFICATION OF CRUDE LYSATES OF IFN X601

| Fraction | IFN Activity* Daudi | HEp-2** | HLA DR |
|---|---|---|---|
| Anti IFN-Beta Column | | | |
| 3 | 3.00 | Not done | 2.3 |
| 4 | 3.25 | 2.89 | 2.3 |
| 5 | 4.25 | 3.79 | 2.47 |
| 6 | 4.20 | 3.85 | 2.65 |
| 7 | 3.82 | 3.25 | Not done |
| Anti IFN Gamma Column | | | |
| 3 | 3.24 | 2.72 | 2.3 |
| 4 | 3.72 | 4.31 | 2.4 |

TABLE 8-continued

MONOCLONAL ANTIBODY AFFINITY
PURIFICATION OF CRUDE LYSATES OF IFN X601

| Fraction | IFN Activity* | | |
|---|---|---|---|
| | Daudi | HEp-2** | HLA DR |
| 5 | 3.70 | 4.15 | 2.3 |
| 6 | 3.28 | 3.95 | 2.3 |
| 7 | 3.22 | 3.67 | Not done |

*Log units/ml = dilution of IFN at 50% assay end point.
**Enhanced antiproliferative activity seen.

TABLE 9

BIOLOGICAL ACTIVITY OF IFN X602
COMPARED WITH IFN X601

| IFN | Antiviral EMC/Vero | Antiproliferative HEp-2 | Daudi | HLA DR Induction Lung Fibroblasts | ELISA | | |
|---|---|---|---|---|---|---|---|
| | | | | | Beta | Gamma | Mixed |
| X601 | 6.49 | 4.74* | 4.28 | 3.30 | 5.93 | 4.08 | 3.50 |
| X602 | 6.46 | 3.89* | 3.55 | 2.81 | 5.94 | 3.46 | 2.75 |

Antiviral plus Beta and Gamma ELISA activities expressed as Log IU/ml/10 A670.
Antiproliferative, HLA DR and Mixed ELISA activities expressed as Log dilution/ml/10 A670 at 50% end point.
1. Assayed in presence of anti IFN beta monoclonal antibody to overcome inhibitory activity of the X430 domain.
*Enhanced growth inhibitory activity typical of IFN gamma/IFN X430 mixtures.

TABLE 10

BIOLOGICAL ACTIVITY OF IFN X603

| IFN | Anitviral EMC/Vero | Antiproliferative | | HLA DR Induction Lung Fibroblasts | ELISA Gamma |
|---|---|---|---|---|---|
| | | HEp-2 | L Cell | | |
| X603 | 4.47 | 3.19 | 4.02 | 2.80 | 4.31 |

Antiviral and Gamma ELISA activities expressed as Log IU/ml/10 A670. Antiproliferative and HLA DR activities express as Log dilution/ml/10 A670 at 50% end point.

What is claimed is:

1. A composition of the formula $$R_1-L-R_2$$

wherein $R_1$ is gamma interferon or a biologically active modified gamma interferon which has one of the following activities:
(a) the ability to protect Vero cells against the cytopathic effect of encephalomyocarditis virus infection; or
(b) antiproliferative activity against HEp-2 cells;
(c) an immunomodulating activity of native gamma interferon;

$R_2$ is human lymphotoxin or a biologically active modified human lymphotoxin which retains a biological activity of native human lymphotoxin; and L is a peptide linker segment of from about 1 to about 500 amino acid residues wherein the L retains or potentiates the biological activity of R1 and/or R2.

2. A composition according to claim 1 wherein L is methionine.

3. A composition according to claim 1 wherein L is mouse IgG 2b "hinge" with each of the four cysteines replaced by serine.

4. A composition according to claim 1 wherein $R_1$ is gamma interferon.

5. A composition according to claim 1 wherein $R_2$ is human lymphotoxin.

6. A composition according to claim 1 wherein $R_1$ is gamma interferon, $R_2$ is human lymphotoxin, and L is a peptide linker segment of from about 1 to about 500 amino acid residues.

7. A composition according to claim 6 wherein L is methionine.

8. A composition according to claim 6 wherein L is mouse IgG 2b "hinge" with each of the four cysteines replaced by serine.

9. The protein identified in FIG. 12 and FIG. 13 as IFNX 603 and having the amino acid sequence shown in FIG. 12 and FIG. 13.

10. The protein identified in FIG. 14 and FIG. 15 as IFNX 604 and having the amino acid sequence shown in FIG. 14 and FIG. 15.

11. A pharmaceutical composition comprising a therapeutically effective amount of a composition of the formula $$R_1-L-R_2$$

wherein $R_1$ is gamma interferon or a biologically active modified gamma interferon which has one of the following activities:
(a) the ability to protect Vero cells against the cytopathic effect of encephalomyocarditis virus infection; or
(b) antiproliferative activity against HEp-2 cells;
(c) an immunomodulating activity of native gamma interferon;

$R_2$ is human lymphotoxin or a biologically active modified human lymphotoxin which retains a biological activity of native human lymphotoxin; and L is a peptide linker segment of from about 1 to about 500 amino acid residues wherein the L retains or potentiates the biological activity of R1 and/or R2 admixed with a pharmaceutically acceptable carrier.

12. A pharmaceutical composition comprising a therapeutically effective amount of the composition of claim 2 admixed with a pharmaceutically acceptable carrier.

13. A pharmaceutical composition comprising a therapeutically effective amount of the composition of claim 3 admixed with a pharmaceutically acceptable carrier.

14. A pharamaceutical composition comprising a therapeutically effective amount of the composition of claim 9 admixed with a pharmaceutically acceptable carrier.

15. A pharmaceutical composition comprising a therapeutically effective amount of the composition of claim 10 admixed with a pharmaceutically acceptable carrier.

16. A method of treating viral infections in an animal in need of such treatment comprising the administration of an effective therapeutic amount of the composition of claim 1.

17. A method of regulating cell growth in an animal in need of such treatment comprising the administration of an effective therapeutic amount of the composition of claim 1.

18. A method of regulating the immune system in an animal in need of such treatment comprising the administration of an effective therapeutic amount of the composition of claim 1.

19. A method of treating viral infections in an animal in need of such treatment comprising the administration of an effective therapeutic amount of the composition of claim 2.

20. A method of regulating cell growth in an animal in need of such treatment comprising the administration of an effective therapeutic amount of the composition of claim 2.

21. A method of regulating the immune system in an animal in need of such treatment comprising the administration of an effective therapeutic amount of the composition of claim 2.

22. A method of treating viral infections in an animal in need of such treatment comprising the administration of an effective therapeutic amount of the composition of claim 3.

23. A method of regulating cell growth in an animal in need of such treatment comprising the administration of an effective therapeutic amount of the composition of claim 3.

24. A method of regulating the immune system in an animal in need of such treatment comprising the administration of an effective therapeutic amount of the composition of claim 3.

25. A method of treating viral infections in an animal in need of such treatment comprising the administration of an effective therapeutic amount of the composition of claim 9.

26. A method of regulating cell growth in an animal in need of such treatment comprising the administration of an effective therapeutic amount of the composition of claim 9.

27. A method of regulating the immune system in an animal in need of such treatment comprising the administration of an effective therapeutic amount of the composition of claim 9.

28. A method of treating viral infections in an animal in need of such treatment comprising the administration of an effective therapeutic amount of the composition of claim 10.

29. A method of regulating cell growth in an animal in need of such treatment comprising the administration of an effective therapeutic amount of the composition of claim 10.

30. A method of regulating the immune system in an animal in need of such treatment comprising the administration of an effective therapeutic amount of the composition of claim 10.

* * * * *

UNITED STATES PATENT AND TRADEMARK OFFICE
CERTIFICATE OF CORRECTION

PATENT NO. : 5,114,711    Page 1 of 3

DATED : May 19, 1992

INVENTOR(S) : Leslie D. Bell, et al

Figure 6:
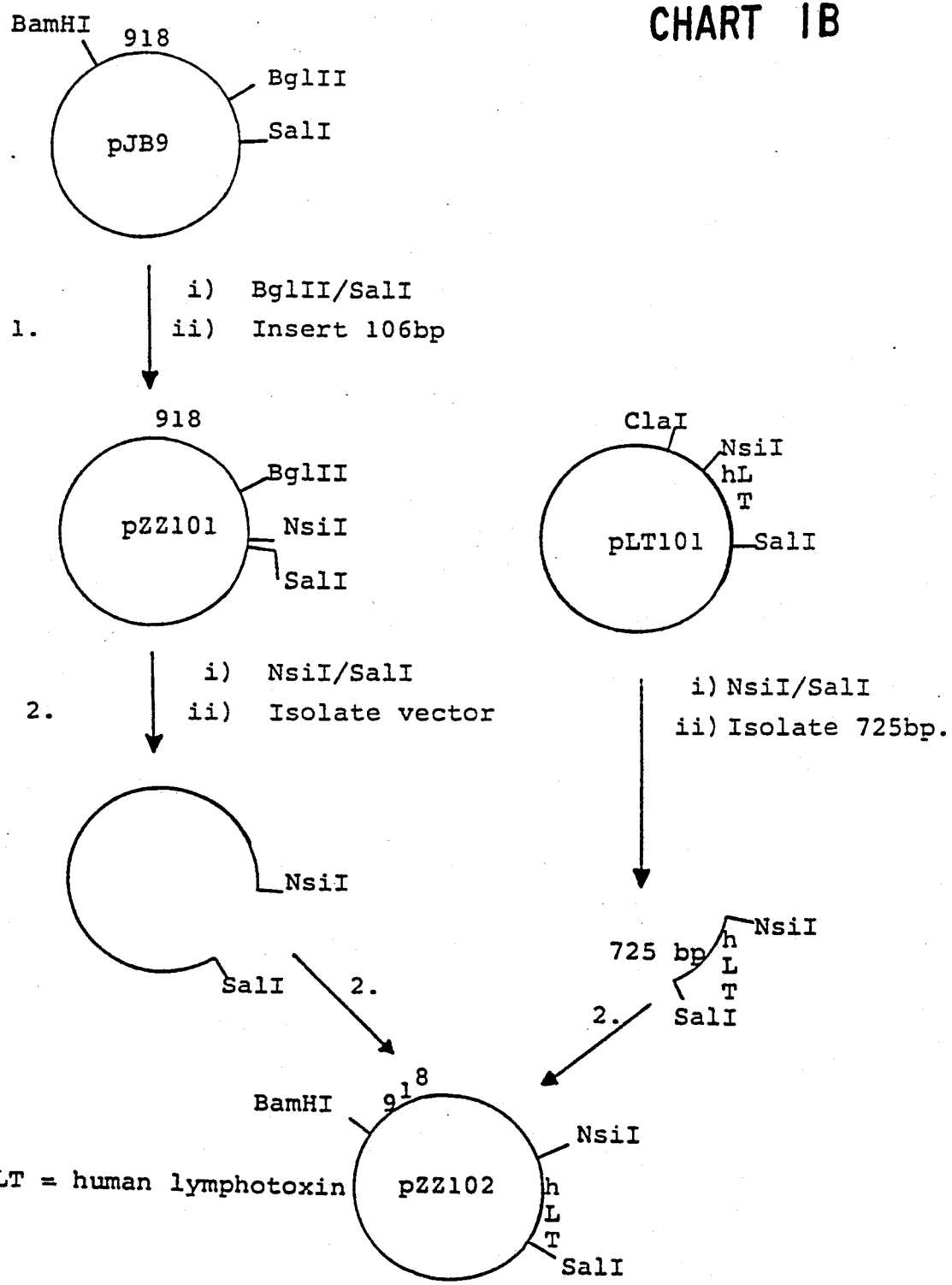
Figure 17:
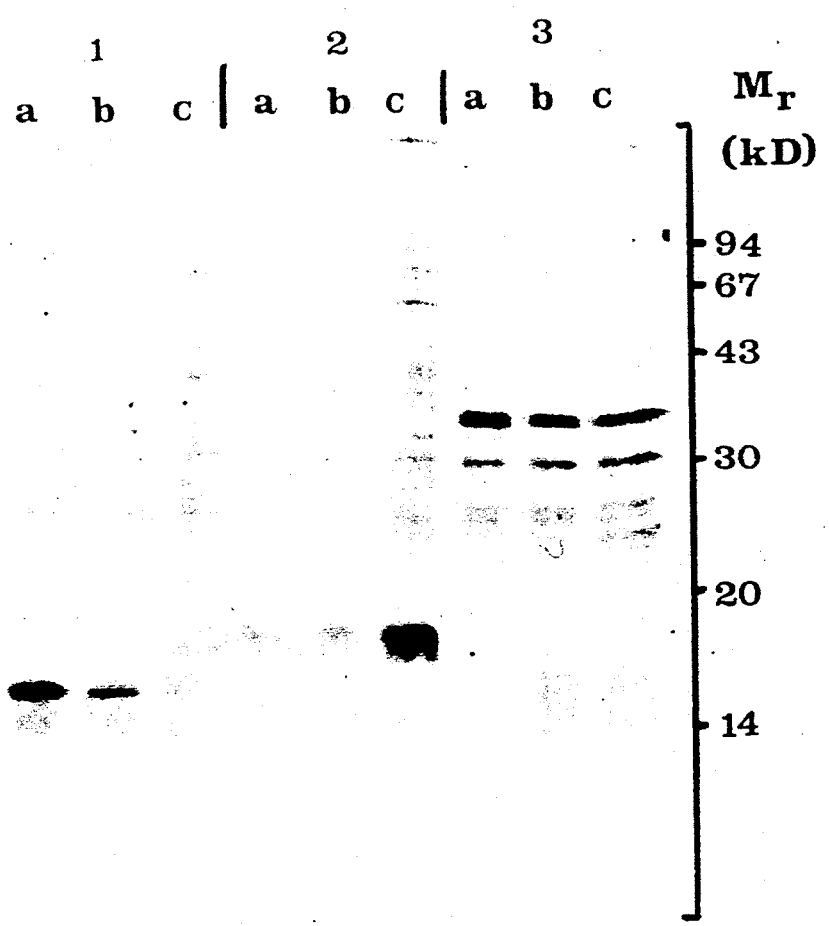
Figure 19:
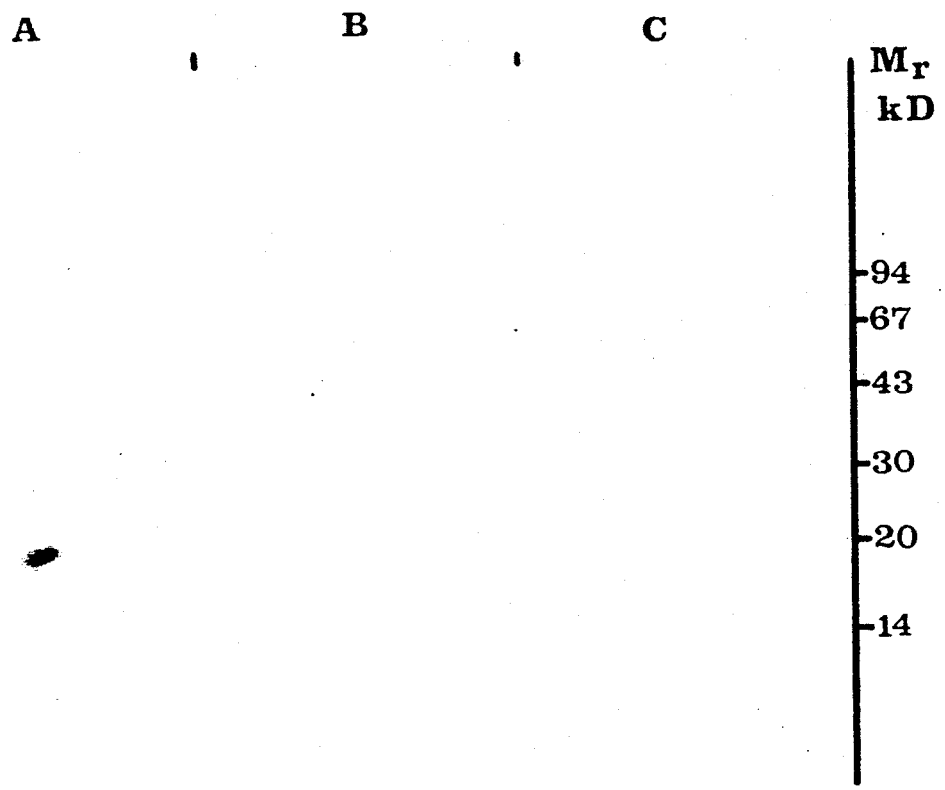

It is certified that error appears in the above-indentified patent and that said Letters Patent is hereby corrected as shown below:

In the Drawings:

Fig. 6, last drawing, reading "HLT" should read -- hLT --.

Chart 5, #188, reading "STG" should read -- CTG --.

Column 4, line 67, reading "type of by" should read -- type or by --.

Column 5, line 22, reading "are replaces by" should read -- are replaced by --.

Column 8, line 61, reading "ATG" should read -- A T G --.

Column 8, line 61, reading "TAG" should read -- T A G --.

Column 8, line 61, reading "(ATG-" should read -- (ATG- --.

Column 8, line 62, reading "TAG" should read -- TAG --.

Column 11, line 3, reading "modulator functionally" should read -- modulator is functionally --.

Column 11, line 14, reading "Res. 4." should read -- Res. 4 --.

Column 11, line 37, reading "shows the equivalent" should read -- shows that equivalent --.

Column 16, line 6, reading "10, 6487," should read -- 10, 6487, --.

UNITED STATES PATENT AND TRADEMARK OFFICE
CERTIFICATE OF CORRECTION

PATENT NO. : 5,114,711

DATED : May 19, 1992

INVENTOR(S) : Leslie D. Bell, et al

Page 2 of 3

It is certified that error appears in the above-indentified patent and that said Letters Patent is hereby corrected as shown below:

Column 16, line 12, reading "Total plasmid" should read -- *Total* plasmid --.

Column 16, line 14, reading "XhoI" should read -- *Xho*I --.

Column 16, line 15, reading "XhoI" should read -- *Xho*I --.

Column 16, line 22, reading "XhoI" should read -- *Xho*I --.

Column 16, line 24, reading "XhoI" should read -- *Xho*I --.

Column 16, line 28, reading "BglII-BamHI" should read -- *Bgl*II-*Bam*HI --.

Column 16, line 33, reading "ClaI-XhoI" should read -- *Cla*I-*Xho*I --.

Column 17:
Table 1, line 21, reading "Nature 312" should read -- Nature *312* --.

Column 17:
Table 2, line 38, reading "X430$^-$" should read -- X430$^+$ --.

UNITED STATES PATENT AND TRADEMARK OFFICE
CERTIFICATE OF CORRECTION

PATENT NO. : 5,114,711
DATED : May 19, 1992
INVENTOR(S) : Leslie D. Bell, et al

It is certified that error appears in the above-indentified patent and that said Letters Patent is hereby corrected as shown below:

Column 18:
Table 5, line 14, reading "IFN-gamma⁻" should read -- IFN-gamma⁺ --.

Table 5, line 26, reading "IFN e.g." should read -- IFN 9(e.g. --.

Signed and Sealed this

Twenty-fifth Day of January, 1994

Attest:

BRUCE LEHMAN

Attesting Officer

Commissioner of Patents and Trademarks